(12) United States Patent
Wu et al.

(10) Patent No.: US 6,946,025 B2
(45) Date of Patent: Sep. 20, 2005

(54) PROCESS FOR PREPARING TETRA-AMIDE COMPOUNDS

(75) Inventors: Bo Wu, Wilsonville, OR (US); Michael B. Meinhardt, Salem, OR (US); Jeffery H. Banning, Hillsboro, OR (US); Donald R. Titterington, Newberg, OR (US)

(73) Assignee: Xerox Corporation, Stamford, CT (US)

( * ) Notice: Subject to any disclaimer, the term of this patent is extended or adjusted under 35 U.S.C. 154(b) by 142 days.

(21) Appl. No.: 10/691,255

(22) Filed: Oct. 22, 2003

(65) Prior Publication Data

US 2005/0090690 A1 Apr. 28, 2005

(51) Int. Cl.$^7$ .......................... C09D 11/12; C07C 231/00
(52) U.S. Cl. ............................... 106/31.29; 106/31.61; 106/31.43; 106/31.75; 106/31.85; 106/31.86; 564/138
(58) Field of Search ........................ 106/31.29, 31.61, 106/31.43, 31.75; 564/138

(56) References Cited

U.S. PATENT DOCUMENTS

| | | | |
|---|---|---|---|
| 3,622,604 A | 11/1971 | Drawert et al. | 260/404.5 |
| 3,653,932 A | 4/1972 | Berry et al. | 106/22 |
| 4,001,186 A | 1/1977 | Onder | 260/63 N |
| 4,061,622 A | 12/1977 | Onder | 260/78 R |
| 4,066,585 A | 1/1978 | Schepp et al. | 260/18 N |
| 4,129,715 A | 12/1978 | Chen et al. | 528/67 |
| 4,156,065 A | 5/1979 | Onder et al. | 528/51 |
| 4,390,369 A | 6/1983 | Merritt et al. | 106/31 |
| 4,395,531 A | 7/1983 | Toyoda et al. | 528/49 |
| 4,417,002 A | 11/1983 | Liessem | 521/128 |
| 4,484,948 A | 11/1984 | Merritt et al. | 106/31 |
| 4,684,956 A | 8/1987 | Ball | 346/1.1 |
| 4,830,671 A | 5/1989 | Frihart et al. | 106/27 |
| 4,851,045 A | 7/1989 | Taniguchi | 106/31 |
| 4,889,560 A | 12/1989 | Jaeger et al. | 106/27 |
| 4,889,761 A | 12/1989 | Titterington et al. | 428/195 |
| 5,006,170 A | 4/1991 | Schwarz et al. | 106/20 |
| 5,151,120 A | 9/1992 | You et al. | 106/27 |
| 5,194,638 A | 3/1993 | Frihart et al. | 554/47 |
| 5,221,335 A | 6/1993 | Williams et al. | 106/23 |
| 5,260,483 A | 11/1993 | Davis et al. | 564/218 |
| 5,372,852 A | 12/1994 | Titterington et al. | 427/288 |
| 5,496,879 A | 3/1996 | Griebel et al. | 524/320 |
| 5,621,022 A | 4/1997 | Jaeger et al. | 523/161 |
| 5,645,632 A | 7/1997 | Pavlin | 106/31.29 |
| 6,133,353 A | 10/2000 | Bui et al. | 524/198 |
| 6,174,937 B1 | 1/2001 | Banning et al. | 523/160 |
| 6,528,613 B1 | 3/2003 | Bui et al. | 528/288 |

FOREIGN PATENT DOCUMENTS

| | | |
|---|---|---|
| EP | 0187352 | 7/1986 |
| EP | 0206286 | 12/1986 |
| WO | WO 94/04619 | 3/1994 |

OTHER PUBLICATIONS

English Abstract for German Publication DE 4205636AL, Aug. 1995.
English Abstract for German Publication DE 4205713AL, 3, 1996.
"The Condensation Reaction Between Isocyanates and Carboxylic Acids. A practical Synthesis of Substituted Amides and Anilides," I. S. Blagbrough et al., *Tetrahedron Letters*, vol. 27, No. 11, pp. 1251–1254 (1996), no month available.
The Chemistry of Amides, Ed. J. Zabicky, p. 155 (Interscience Publishers 1970), no month available.
K. B. Onder et al., "Thermoplastic Copolyamides from 4,4'–Methylene bis(Phenyl Isocyanate)," *Polymer Preprints*, 21(2), p. 132 (1980), no month available.
"Synthesis of Polymers from Isocyanates in Polar Solvents," H. Ulrich, *J. Polymer Sci.: Macromolar Reviews*, vol. 11, 93–133 (1976), no month available.
Polyurethanes: Chemistry and Technology, Part I, J. H. Saunders & K. C. Frish, Interscience Publishers, p. 79 and p. 187 (John Wiley & Sons 1962), no month available.

*Primary Examiner*—J. A. Lorengo
*Assistant Examiner*—Veronica F. Faison

(57) ABSTRACT

Disclosed is a process for preparing a tetra-amide which comprises carrying out a condensation reaction between a diacid, a monoacid, and a diisocyanate, thereby forming a tetra-amide. Also disclosed is a process for preparing a phase change ink composition which comprises (a) carrying out a condensation reaction between a diacid, a monoacid, and a diisocyanate, thereby forming a tetra-amide; and (b) admixing the tetra-amide thus formed with a colorant, thereby forming a phase change ink.

75 Claims, No Drawings

PROCESS FOR PREPARING TETRA-AMIDE COMPOUNDS

BACKGROUND

Disclosed herein are methods for preparing components suitable for use in phase change inks. More specifically, disclosed herein are processes for preparing tetra-amide compounds suitable as components in phase change ink carriers. One specific embodiment is directed to a process for preparing a tetra-amide which comprises carrying out a condensation reaction between a diacid, a monoacid, and a diisocyanate, thereby forming a tetra-amide. Another specific embodiment is directed to a process for preparing a phase change ink composition which comprises (a) carrying out a condensation reaction between a diacid, a monoacid, and a diisocyanate, thereby forming a tetra-amide; and (b) admixing the tetra-amide thus formed with a colorant, thereby forming a phase change ink.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 6,133,353 (Bui et al.), the disclosure of which is totally incorporated herein by reference, discloses a solubilizing agent and a compound made by reacting selected nucleophiles, including fatty acid reactants and amines with an isocyanate. The addition of the isocyanate and the different nucleophiles will create a di-urethane tetra-amide solubilizing agent product. The polyamide-solubilizing agent is useful as an ingredient in a phase change solid imaging material and as carrier compositions used to make phase change ink jet inks.

U.S. Pat. No. 6,528,613 (Bui et al.), the disclosure of which is totally incorporated herein by reference, discloses a solubilizing agent and a compound made by reacting selected nucleophiles, including fatty acid reactants and amines with an isocyanate. The addition of the isocyanate and the different nucleophiles will create a di-urethane tetra-amide solubilizing agent product. The polyamide-solubilizing agent is useful as an ingredient in a phase change solid imaging material and as carrier compositions used to make phase change ink jet inks.

U.S. Pat. No. 4,830,671 (Frihart et al.), the disclosure of which is totally incorporated herein by reference, discloses an ink composition having the properties of stability and uniformity of performance under ink jet printing conditions and desired printing properties which can be obtained with hot melt ink compositions consisting of a resinous binder comprised of a compound of the formula

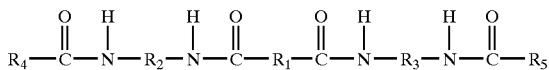

wherein $R_1$ represents a polymerized fatty acid residue with two carboxylic acid groups removed, $R_2$ and $R_3$ are the same or different and each represent an alkylene with up to 12 carbon atoms, a cycloalkylene with 6 to 12 carbon atoms, an arylene with 6 to 12 carbon atoms, or an alkarylene with 7 to 12 carbon atoms, and $R_4$ and $R_5$ are the same or different and each represents an alkyl having up to 36 carbon atoms, a cycloalkyl having up to 36 carbon atoms and aryl having up to 36 carbon atoms, or an alkaryl having up to 36 carbon atoms, said resinous binder having a melt viscosity of less than 250 CPS at 50° C. and a colorant distributed through the resinous binder in an effective amount sufficient to impart a predetermined color to the resulting hot melt ink composition.

U.S. Pat. No. 5,194,638 (Frihart et al.), the disclosure of which is totally incorporated herein by reference, discloses a resinous binder for use in hot melt ink compositions, which ink compositions may be used in hot melt ink jet printing applications. The resinous binder has a melt viscosity of 250 cps or less at 150° C., is sufficiently transparent to allow a colorant to be distributed through the resinous binder in an amount effective to impart a pre-determined color to the resulting hot melt ink composition, and has a blocking temperature greater than 100° C.

U.S. Pat. No. 5,645,632 (Pavlin), the disclosure of which is totally incorporated herein by reference, discloses solid diesters for hot-melt inks which are prepared by reaction of polymerized fatty acid with long chain primary monohydric alcohols, optionally in the presence of diamine. The long chain alcohols have at least about 20 carbon atoms, and preferably have 24 or more carbon atoms. The esterification of liquid polymerized fatty acid with monohydric alcohol provides a diester that is solid at room temperature and has a melting point of less than about 150° C. The diester can be formulated with colorants and/or other image-producing materials to provide an ink for hot-melt printing, e.g., hot-melt ink jet, gravure or intaglio printing.

U.S. Pat. No. 6,174,937 (Banning et al.), the disclosure of which is totally incorporated herein by reference, discloses a phase change ink comprising a material of the formula

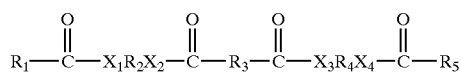

wherein $X_1$, $X_2$, $X_3$, and $X_4$ are segments comprising atoms selected from groups V and VI of the periodic table; wherein at least one $R_1$ and $R_5$ comprises at least 37 carbon units; and wherein $R_2$, $R_3$, and $R_4$ each comprise at least one carbon unit. The invention further encompasses a composition of matter, as well as methods of reducing coefficients of friction of phase change ink formulations.

U.S. Pat. No. 4,889,560 (Jaeger et al.), the disclosure of which is totally incorporated herein by reference, discloses a phase change ink carrier composition combined with a compatible colorant to form a phase change ink composition. A thin film of substantially uniform thickness of that phase change ink carrier composition, and the ink produced therefrom, has a high degree of lightness and chroma. The thin films of a substantially uniform thickness of the ink composition are also rectilinearly light transmissive. The carrier composition is preferably a fatty amide-containing compound.

U.S. Pat. No. 5,372,852 (Titterington et al.), the disclosure of which is totally incorporated herein by reference, discloses a phase change ink composition that is indirectly applied to a substrate by raising the temperature of the phase change ink composition to form a liquid phase change ink composition, applying droplets of the phase change ink composition in a liquid phase to a liquid intermediate transfer surface on a solid support in a pattern using a device such as an ink jet printhead, solidifying the phase change ink composition on the liquid intermediate transfer surface, transferring the phase change ink composition from the liquid intermediate transfer surface to the substrate, and fixing the phase change ink composition to the substrate. The phase change ink composition is malleable when the ink is transferred from the intermediate transfer surface to the substrate and is ductile after the ink has been transferred to the substrate and cooled to ambient temperature to preclude the ink from crumbling and cracking.

U.S. Pat. No. 5,260,483 (Davis et al.), the disclosure of which is totally incorporated herein by reference, discloses methods of producing N-aryl amides which comprise reacting an aromatic isocyanate compound with substantially anhydrous carboxylic acid and recovering the resulting N-aryl amide. Additionally, or alternatively, methods of forming N-aryl amides comprise reacting an aromatic isocyanate compound with substantially anhydrous carboxylic acid in the presence of an anhydrous hydrogen halide or hydrolytically unstable halide compound and recovering the resulting N-aryl amide. These reactions may occur in the presence of an aprotic solvent.

U.S. Pat. No. 4,001,186 (Onder), the disclosure of which is totally incorporated herein by reference, discloses the use of certain catalysts that provide for an improved process for the preparation of soluble polyimides, polyamides, and polyamideimides. The catalysts are alkali metal salts of formula MOR, wherein R represents alkyl or aryl and M represents an alkali metal. The improved process comprises reacting organic diisocyanates with polycarboxylic compounds consisting of tetracarboxylic acids or the intramolecular dianhydrides thereof, tricarboxylic acids or the monoanhydrides thereof, dicarboxylic acids, and mixtures thereof, in the presence of said catalysts. The polymers are obtained in solution at low reaction temperatures and short reaction times thereby avoiding side-reactions which otherwise would be detrimental to polymer molecular weight and ultimate polymer properties.

U.S. Pat. No. 4,129,715 (Chen et al.), the disclosure of which is totally incorporated herein by reference, discloses substantially linear, segmented polyester amides which contain aromatic residues in the "hard" segments but which still possess sufficiently low melt properties to be injection moldable. The polyester amides are obtained by reacting a carboxylic acid-terminated prepolymer (derived by reacting an excess of a dicarboxylic acid with a polymeric diol of molecular weight 400 to 4000) with a stoichiometric amount of methylenebis[]phenyl isocyanate) or toluene diisocyanate or mixtures of these isocyanates and, optionally, a dicarboxylic acid.

U.S. Pat. No. 4,395,531 (Toyoda et al.), the disclosure of which is totally incorporated herein by reference, discloses a process for the preparation of polyamide compounds by reacting at least one polycarboxylic acid with at least one diisocyanate in the presence of a catalyst comprising at least one mono-alkali metal salt of dicarboxylic acid. The polyamide compounds prepared by this process have a substantially linear configuration and a high degree of polymerization and, therefore, are suitable for the manufacture of fibers, films and molded articles.

U.S. Pat. No. 4,156,065 (Onder et al.), the disclosure of which is totally incorporated herein by reference, discloses an improved process for the reaction of an isocyanate (mono or poly) with a carboxylic acid or anhydride (mono or poly) to form the corresponding imide, amide or amide-imides. The improvement lies in using as the catalyst the 1-oxide, 1-sulfide or 1-hydrocarbylimino derivative of a phospholene, phospholane or phosphetane. The latter compounds are also substituted in the 1-position by a hydrocarbyl ($C_{1-12}$) or halohydrocarbyl ($C_{1-12}$) and may additionally carry one or more halo, lower-alkoxy, phenoxy, lower-hydrocarbyl or halo-substituted hydrocarbyl groups on the ring carbon atoms.

U.S. Pat. No. 4,061,622 (Onder), the disclosure of which is totally incorporated herein by reference, discloses the use of certain catalysts that provide for an improved process for the preparation of soluble polyimides, polyamides, and polyamideimides. The catalysts are alkali metal salts of formula MOR, wherein R represents alkyl or aryl and M represents an alkali metal. The improved process comprises reacting organic diisocyanates with polycarboxylic compounds consisting of tetracarboxylic acids or the intramolecular dianhydrides thereof, tricarboxylic acids or the monoanhydrides thereof, dicarboxylic acids, and mixtures thereof, in the presence of said catalysts. The polymers are obtained in solution at low reaction temperatures and short reaction times thereby avoiding side-reactions which otherwise would be detrimental to polymer molecular weight and ultimate polymer properties.

U.S. Pat. No. 4,066,585 (Schepp et al.), the disclosure of which is totally incorporated herein by reference, discloses intaglio and flexographic printing processes employing solvent-free inks, solid at room temperature but molten at printing temperatures, and inks suitable therefor, said inks comprising a pigment and a thermoplastic binder having a softening point between 90° C. and 160° C., said binder comprising a synthetic polyamide resin or synthetic polyesteramide resin, each resin being the condensation product of (1) an acid component comprising a dimerized fatty acid and a monocarboxylic acid and (2) an amine component comprising a diamine and, in the case of the polyesteramide resin, additionally comprising a diol and/or alkanolamine.

U.S. Pat. No. 3,622,604 (Drawert et al.), the disclosure of which is totally incorporated herein by reference, discloses synthetic polyamides, useful as binders in the formulation of printing inks, formed between a dimeric fatty acid, an unsubstituted lower aliphatic monocarboxylic acid, ethylene diamine, and certain aromatic, cycloaliphatic, and other aliphatic diamines, including aliphatic ether diamines, and methods for preparing such amides.

U.S. Pat. No. 4,417,002 (Liessem), the disclosure of which is totally incorporated herein by reference, discloses a process wherein a carboxylic acid or carboxylate is reacted with an isocyanate to produce gas which is used to give a blowing action in the manufacture of a foam plastics material, especially foam polyurethane. Preferably formic acid or a formate is used.

"The Condensation Reaction Between Isocyanates and Carboxylic Acids. A practical Synthesis of Substituted Amides and Anilides," I. S. Blagbrough et al., *Tetrahedron Letters*, Vol. 27, No. 11, pp. 1251–1254 (1996), the disclosure of which is totally incorporated herein by reference, discloses that addition of a carboxylic acid to an isocyanate initially yields the mixed acid anhydride, decarboxylation of which leads to the N-substituted amide. The conversion of acid into amide was shown to proceed similarly for both aliphatic and aromatic carboxylic acids with a range of substituted isocyanates.

*The Chemistry of Amides*, Ed. J. Zabicky, p. 155 (Interscience Publishers 1970), the disclosure of which is totally incorporated herein by reference, discloses reactions between isocyanates and carboxylic acids.

K. B. Onder et al., "Thermoplastic Copolyamides from 4,4'-Methylene bis(Phenyl Isocyanate)," *Polymer Preprints*, 21(2), p. 132 (1980), the disclosure of which is totally incorporated herein by reference, discloses the synthesis of aromatic diamine based polyamides using aromatic diisocyanates and dicarboxylic acids.

"Synthesis of Polymers from Isocyanates in Polar Solvents," H. Ulrich, *J. Polymer Sci.: Macromolor Reviews*, Vol. 11, 93–133 (1976), the disclosure of which is totally incorporated herein by reference, discloses the preparation of various kinds of polymers from isocyanates.

*Preparative Methods of Polymer Chemistry*, 2nd Ed., W. Sorenson, p.102 (Interscience Publishers 1969), the disclosure of which is totally incorporated herein by reference, discloses the preparation of polyamides from diisocyanates and dicarboxylic acids.

*Polyurethanes: Chemistry and Technology, Part I*, J. H. Saunders & K. C. Frish, Interscience Publishers, p. 79 and p. 187 (John Wiley & Sons 1962), the disclosure of which is totally incorporated herein by reference, discloses reactions between isocyanates and carboxylic acids.

In many known methods for preparing tetra-amides, such as those which entail condensation reactions between acids and ethylene diamine, the reaction must be carried out at relatively high temperatures, typically about 200° C. or higher. In addition, these reactions generate a hazardous mixture of water (as a result of the condensation) and ethylene diamine.

Accordingly, while known compositions and processes are suitable for their intended purposes, a need remains for improved phase change inks. In addition, a need remains for improved processes for preparing phase change inks. Further, a need remains for improved processes for preparing tetra-amide compounds. Additionally, a need remains for processes for preparing tetra-amide compounds that can be carried out at desirably low temperatures. There is also a need for processes for preparing tetra-amide compounds that do not generate toxic or hazardous materials. There is also a need for processes for preparing tetra-amide compounds that enable desirably high yields under relatively mild reaction conditions.

SUMMARY

Disclosed herein is a process for preparing a tetra-amide which comprises carrying out a condensation reaction between a diacid, a monoacid, and a diisocyanate, thereby forming a tetra-amide. Also disclosed herein is a process for preparing a phase change ink composition which comprises (a) carrying out a condensation reaction between a diacid, a monoacid, and a diisocyanate, thereby forming a tetra-amide; and (b) admixing the tetra-amide thus formed with a colorant, thereby forming a phase change ink.

DETAILED DESCRIPTION

Disclosed herein is a process for preparing a tetra-amide which comprises carrying out a condensation reaction between a diacid, a monoacid, and a diisocyanate, thereby forming a tetra-amide. The diacid is of the general formula

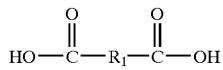

wherein $R_1$ is (i) an alkylene group (including linear, branched, saturated, unsaturated, cyclic, substituted, and unsubstituted alkylene groups, and wherein hetero atoms, such as oxygen, nitrogen, sulfur, silicon, phosphorus, and the like either may or may not be present in the alkylene group provided that no hetero atom is directly bonded to either of the carboxylic acid groups), in one embodiment with at least 1 carbon atom, in another embodiment with at least about 6 carbon atoms, and in yet another embodiment with at least about 34 carbon atoms, and in one embodiment with no more than about 100 carbon atoms, in another embodiment with no more than about 80 carbon atoms, and in yet another embodiment with no more than about 60 carbon atoms, although the number of carbon atoms can be outside of these ranges, (ii) an arylene group (including unsubstituted and substituted arylene groups, and wherein hetero atoms, such as oxygen, nitrogen, sulfur, silicon, phosphorus, and the like either may or may not be present in the arylene group provided that no hetero atom is directly bonded to either of the carboxylic acid groups), in one embodiment with at least about 6 carbon atoms, in another embodiment with at least about 10 carbon atoms, and in yet another embodiment with at least about 14 carbon atoms, and in one embodiment with no more than about 100 carbon atoms, in another embodiment with no more than about 80 carbon atoms, and in yet another embodiment with no more than about 60 carbon atoms, although the number of carbon atoms can be outside of these ranges, (iii) an arylalkylene group (including unsubstituted and substituted arylalkylene groups, wherein the alkyl portion of the arylalkylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkylene group provided that no hetero atom is directly bonded to either of the carboxylic acid groups), in one embodiment with at least about 7 carbon atoms, in another embodiment with at least about 12 carbon atoms, and in yet another embodiment with at least about 16 carbon atoms, and in one embodiment with no more than about 100 carbon atoms, in another embodiment with no more than about 80 carbon atoms, and in yet another embodiment with no more than about 60 carbon atoms, although the number of carbon atoms can be outside of these ranges, such as benzylene or the like, or (iv) an alkylarylene group (including unsubstituted and substituted alkylarylene groups, wherein the alkyl portion of the alkylarylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylarylene group provided that no hetero atom is directly bonded to either of the carboxylic acid groups), in one embodiment with at least about 7 carbon atoms, in another embodiment with at least about 11 carbon atoms, and in yet another embodiment with at least about 15 carbon atoms, and in one embodiment with no more than about 100 carbon atoms, in another embodiment with no more than about 80 carbon atoms, and in yet another embodiment with no more than about 60 carbon atoms, although the number of carbon atoms can be outside of these ranges, such as tolylene or the like, wherein the substituents on the substituted alkylene, arylene, arylalkylene, and alkylarylene groups can be (but are not limited to) halogen atoms, imine groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, nitro groups, nitroso groups, sulfone groups, acyl groups, azide groups, azo groups, cyanato groups, thiocyanato groups, carboxylate groups, urea groups, mixtures thereof, and the like, wherein two or more substituents can be joined together to form a ring.

Specific examples of suitable diacids include malonic acid, methyl malonic acid, ethyl malonic acid, butyl malonic acid, dimethyl malonic acid, diethyl malonic acid, succinic acid, methyl succinic acid, dimethyl succinic acid, 2-ethyl-2-methyl succinic acid, 2,3-dimethyl succinic acid, glutaric acid, 2-methyl glutaric acid, 3-methyl glutaric acid, 2,2-dimethyl glutaric acid, 3,3-dimethyl glutaric acid, adipic acid, 3-methyl adipic acid, 3-tert-butyl adipic acid, pimelic acid, suberic acid, azelaic acid, sebacic acid, 1,11-undecanedicarboxylic acid, undecanedioic acid, 1,10-decanedicarboxylic acid, 1,12-dodecanedicarboxylic acid, hexadecanedioic acid, docosanedioic acid, tetracosanedioic acid, itaconic acid, maleic acid, fumaric acid, citraconic acid, mesaconic acid, glutaconic acid, β-hydromuconic acid, traumatic acid, muconic acid, aconitic acid, chlorosuccinic acid, bromosuccinic acid, 2,3-dibromosuccinic acid, tetrafluorosuccinic acid, hexafluoroglutaric acid, perfluoroadipic acid, perfluorosuberic acid, 3-chlorododecanedioic acid, dibromomaleic acid, diglycolic acid, 3,6-dioxaoctanedioic acid, thiodiglycolic acid, 3,3'-thiodipropionic acid, 1,3-acetonedicarboxylic acid, 3-oxoadipic acid, 4-ketopimelic acid, 5-oxoazelaic acid, chelidonic acid, 1,2-cyclopentanedicarboxylic acid, 3,3-tetramethyleneglutaric acid, camphoric acid, cyclohexylsuccinic acid, 1,1-cyclohexanediacetic acid, 1,2-cyclohexanedicarboxylic acid, 1,3-cyclohexanedicarboxylic acid, 1,4-cyclohexanedicarboxylic acid, 1,3-adamantanedicarboxylic acid, 1,3-adamantanediacetic acid, 5-norbornene-2,3-dicarboxylic acid, 1,4,5,6,7,7-hexachloro-5-norbornene-2,3-dicarboxylic acid, phenylsuccinic acid, 3-phenylglutaric acid, 1,2-phenylenediacetic acid, 1,2-phenylenedioxydiacetic acid, homophthalic acid, 1,3-phenylenediacetic acid, 4-carboxyphenoxyacetic acid, 1,4-phenylenediacetic acid, 1,4-phenylenedipropionic acid, 2-carboxycinnamic acid, 1,4-phenylenediacrylic acid, 2-carboxybenzenepropanoic acid, 4,4'-(hexafluoroisopropylidene)bis(benzoic acid), 4,4'-oxybis (benzoic acid), phthalic acid, isophthalic acid, terephthalic acid, 3-fluorophthalic acid, 2-methoxyisophthalic acid, 3-nitrophathalic acid, 4-methylphthalic acid, 2-bromoterephthalic acid, 4-bromoisophthalic acid, 4-nitrophthalic acid, nitroterephthalic acid, 5-tert-butylisophthalic acid, 5-octadecyloxyisophthalic acid, 5-nitroisophthalic acid, 4,5-dichlorophthalic acid, tetrafluoroterephthalic acid, tetrafluoroisophthalic acid, tetrafluorophthalic acid, diphenic acid, 4,4'-biphenyidicarboxylic acid, 4-[4-(2-carboxybenzoyl)phenyl]butyric acid, 1,4-naphthalenedicarboxylic acid, 2,3-naphthalenedicarboxylic acid, 2,6-naphthalenedicarboxylic acid, 2,7-di-tert-butyl-9,9-dimethyl-4,5-xanthenedicarboxylic acid, phenylmalonic acid, benzylmalonic acid, PRIPOL 1006, which is a dimer acid commercially available from Uniqema, Chicago, Ill., believed to be of the general formula

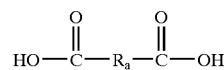

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10, and more specifically believed to include isomers of the formula

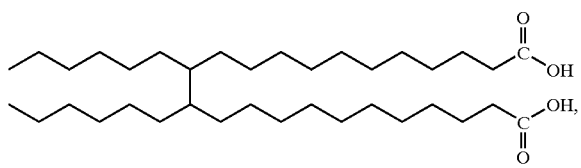

and the like, as well as mixtures thereof.

The monoacid is of the general formula

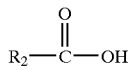

wherein $R_2$ is (i) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group provided that no hetero atom is directly bonded to the carboxylic acid group), in one embodiment with at least 1 carbon atom, in another embodiment with at least about 3 carbon atoms, and in yet another embodiment with at least about 6 carbon atoms, and in one embodiment with no more than about 300 carbon atoms, in another embodiment with no more than about 200 carbon atoms, and in yet another embodiment with no more than about 150 carbon atoms, although the number of carbon atoms can be outside of these ranges, (ii) an aryl group (including unsubstituted and substituted aryl groups, and wherein hetero atoms, such as oxygen, nitrogen, sulfur, silicon, phosphorus, and the like either may or may not be present in the aryl group provided that no hetero atom is directly bonded to the carboxylic acid group), in one embodiment with at least about 6 carbon atoms, in another embodiment with at least about 10 carbon atoms, and in yet another embodiment with at least about 14 carbon atoms, and in one embodiment with no more than about 300 carbon atoms, in another embodiment with no more than about 200 carbon atoms, and in yet another embodiment with no more than about 150 carbon atoms, although the number of carbon atoms can be outside of these ranges, (iii) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group provided that no hetero atom is directly bonded to the carboxylic acid group), in one embodiment with at least about 7 carbon atoms, in another embodiment with at least about 11 carbon atoms, and in yet another embodiment with at least about 15 carbon atoms, and in one embodiment with no more than about 300 carbon atoms, in another embodiment with no more than about 200 carbon atoms, and in yet another embodiment with no more than about 150 carbon atoms, although the number of carbon atoms can be outside of these ranges, such as benzyl or the like, or (iv) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group provided that no hetero atom is directly bonded to the carboxylic acid group), in one embodiment with at least about 7 carbon atoms, in another embodiment with at least about 11 carbon atoms, and in yet another embodiment with at least about 15 carbon atoms, and in one embodiment with no more than about 300 carbon atoms, in another embodiment with no more than about 200 carbon atoms, and in yet another embodiment with no more than about 150 carbon atoms, although the number of carbon atoms can be outside of these ranges, such as tolyl or the like, wherein the substituents on the substituted alkyl, aryl, arylalkyl, and alkylaryl groups can be (but are not limited to) halogen atoms, imine groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, nitro groups, nitroso groups, sulfone groups, acyl groups, azide groups, azo groups, cyanato groups, thiocyanato groups, carboxylate groups, urea groups, mixtures thereof, and the like, wherein two or more substituents can be joined together to form a ring.

Specific examples of suitable monoacids include acetic acid, propionic acid, butyric acid, valeric acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, eicosanoic acid, heneicosanoic acid, docosanoic acid, tricosanoic acid, tetracosanoic acid, hexacosanoic acid, heptacosanoic acid, octacosanoic acid, triacontanoic acid, isobutyric acid, 2-ethylbutyric acid, trimethylacetic acid, 2-methylbutyric acid, isovaleric acid, 2,2-dimethylbutyric acid, tert-butylacetic acid, 2-methylvaleric acid, 2-propylpentanoic acid, 3-methylvaleric acid, 4-methylvaleric acid, 2-methylhexanoic acid, 2-ethylhexanoic acid, acrylic acid, methacrylic acid, crotonic acid, vinylacetic acid, tiglic acid, 3,3-dimethylacrylic acid, 2-pentenoic acid, 4-pentenoic acid, 2-methyl-2-pentenoic acid, 2,2-dimethyl-4-pentenoic acid, 2-hexenoic acid, 3-hexenoic acid, 2-ethyl-2-hexenoic acid, 6-heptenoic acid, 2-octenoic acid, citronellic acid, undecylenic acid, myristoleic acid, palmitoleic acid, oleic acid, elaidic acid, 11-eicosenoic acid, erucic acid, nervonic acid, chloroacetic acid, bromoacetic acid, iodoacetic acid, difluoroacetic acid, dichloroacetic acid, dibromoacetic acid, trifluoroacetic acid, chlorodifluoroacetic acid, trichloroacetic acid, tribromoacetic acid, 2-chloropropionic acid, 3-chloropropionic acid, 2-bromopropionic acid, 3-bromopropionic acid, 2-iodopropionic acid, 3-iodopropionic acid, 2,2-dichloropropionic acid, 2,3-dibromopropionic acid, pentafluoropropionic acid, 2-bromo-2-methylpropionic acid, 3-bromo-2-(bromomethyl)-propionic acid, 3-chloropivalic acid, 3,3-dichloropivalic acid, 4-chlorobutyric acid, 2-bromobutyric acid, 4-bromobutyric acid, heptafluorobutyric acid, 2-bromo-3-methylbutyric acid, 5-chlorovaleric acid, 2-bromovaleric acid, 5-bromovaleric acid, nonafluoropentanoic acid, 2-bromohexanoic acid, 6-bromohexanoic acid, tridecafluoroheptanoic acid, 2-bromooctanoic acid, 8-brommooctanoic acid, pentadecafluorooctanoic acid, heptadecafluorononanoic acid, nonadecafluorodecanoic acid, perfluorosebacic acid, 11-bromoundecanoic acid, 12-bromododecanoic acid, perfluorododecanoic acid, 2-bromotetradecanoic acid, 2-bromohexadecanoic acid, 3-chloroacrylic acid, 2-bromoacrylic acid, 2-(trifluoromethyl)acrylic acid, 2-(bromomethyl)acrylic acid, 4,4,4-trifluoro-3-methyl-2-butenoic acid, methoxyacetic acid, ethoxyacetic acid, 3-methoxypropionic acid, 2-(2- methoxyethoxy)acetic acid, 2-[2-(methoxyethoxy)ethoxy] acetic acid, tetrahydro-2-furoic acid, tetrahydro-3-furoic acid, 2,3,4,6-di-O-isopropylidene-2-ketogluconic acid, 3-nitropropionic acid, 6-nitrocaproic acid, 1 2-nitrododecanoic acid, succinic semialdehyde, levulinic acid, 4-acetylbutyric acid, 6-oxoheptanoic acid, 7-oxooctanoic acid, 4,6-dioxoheptanoic acid, 3,4-dihydro-2,2-dimethyl-4-oxo-2H-pyran-6-carboxylic acid, cyclopentanecarboxylic acid, cyclopentylacetic acid, 3-cyclopentylpropionic acid, 3-methyl-2-(nitromethyl)-5-oxocyclopentaneacetic acid, cyclohexanecarboxylic acid, cyclohexylacetic acid, dicyclohexylacetic acid, cyclohexanepropionic acid, cyclohexanebutyric acid, cyclohexanepentanoic acid, 1-methyl-1-cyclohexanecarboxylic acid, 2-methyl-1-cyclohexanecarboxylic acid, 3-methyl-1-cyclohexanecarboxylic acid, 4-methyl-1-cyclohexanecarboxylic acid, 4-tert-butylcyclohexanecarboxylic acid, 4-pentylcyclohexanecarboxylic acid, 4-methylcyclohexaneacetic acid, 3-methoxycyclohexanecarboxylic acid, 4-methoxycyclohexanecarboxylic acid, cyclohexanecarboxylic acid, 2-norbornaneacetic acid, 4-pentylbicyclo[2.2.2]octane-1-carboxylic acid, 3-oxotricyclo[2.2.1.0(2,6)]-heptane-1-carboxylic acid, 3-noradamantanecarboxylic acid, 1-adamantanecarboxylic acid, 1-adamantaneacetic acid, 1-cyclopentene-1-carboxylic acid, 2-cyclopentene-1-acetic acid, 1-cyclohexene-1-carboxylic acid, 1-methyl-2-cyclohexene-1-carboxylic acid, 1,4-dihydro-2-methylbenzoic acid, retinoic acid, ketopinic acid, abietic acid, phenylacetic acid, 1-phenyl-1-cyclopentanecarboxylic acid, α-phenylcyclopentaneacetic acid, diphenylacetic acid, triphenylacetic acid, 2-phenylpropionic acid, hydrocinnamic acid, α-methylhydrocinnamic acid, α-(tert-butyl)hydrocinnamic acid, 2,2-diphenylpropionic acid, 3,3-diphenylpropionic acid, 3,3,3-triphenylpropionic acid, 2-phenylbutyric acid, 3-phenylbutyric acid, 4-phenylbutyric acid, 5-phenylvaleric acid, 3-methyl-2-phenylvaleric acid, 6-phenylhexanoic acid, α-fluorophenylacetic acid, α-bromophenylacetic acid, α-methoxyphenylacetic acid, phenoxyacetic acid, α,β-dibromohydrocinnamic acid, 3-phenoxypropionic acid, 2-phenoxypropionic acid, 11-phenoxyundecanoic acid, 2-phenoxybutyric acid, α-methoxy-α-(trifluoromethyl) phenylacetic acid(phenylthio)acetic acid, 3-(phenylthio)acrylic acid, benzylthioglycolic acid, 2-ethylthio-2,2-diphenylacetic acid, 3-benzoylpropionic acid, 2-methyl-4-oxo-4-phenylbutyric acid, 4-benzoylbutyric acid, o-tolylacetic acid, 3-oxo-1-indancarboxylic acid, 1,2,3,4-tetrahydro-2-naphthoic acid, (α,α,α-trifluoro-o-tolyl)acetic acid, 2-fluorophenylacetic acid, 2-chlorophenylacetic acid, 2-bromophenylacetic acid, 2-iodophenylacetic acid, 2-(2-chlorophenoxy)propionic acid, 2-methoxyphenylacetic acid, 3-(2-methoxyphenyl)propionic acid, 2-nitrophenylacetic acid, 2-formylphenoxyacetic acid, m-tolylacetic acid, 3-fluorophenylacetic acid, 3-chlorophenylacetic acid, 3-bromophenylacetic acid, 2-(3-chlorophenoxy)propionic acid, (α,α,α-trifluoro-m-tolyl)acetic acid, 3-methoxyphenylacetic acid, 3-nitrophenylacetic acid, p-tolylacetic acid, 3-(p-tolyl)propionic acid, (4-methylphenoxy)acetic acid, 4-isobutyl-α-methylphenylacetic acid, 4-acetylphenoxyacetic acid, 4-(4-chloro-o-tolyloxy)butyric acid, 4-fluorophenylacetic acid, (α,α,α-trifluoro-p-tolyl)acetic acid, 3-(4-fluorobenzoyl) propionic acid, 3-(4-chlorobenzoyl)propionic acid, 4-chlorophenylacetic acid, bis(4-chlorophenyl)acetic acid, 4-bromophenylacetic acid, 3,3,3-tris(4-chlorophenyl) propionic acid, 4-(bromomethyl)phenylacetic acid, 1-(4-chlorophenyl)-1-cyclopentanecarboxylic acid, 4-methoxyphenylacetic acid, 4-ethoxyphenylacetic acid, 3-(4-methoxyphenyl)propionic acid, 4-(4-methoxyphenyl) propionic acid, 4-chlorophenoxyacetic acid, bis(4-chlorophenoxy)acetic acid, 4-(methylthio)-phenylacetic acid, 4-nitrophenylacetic acid, 2-(4-nitrophenyl)propionic acid, 4-(4-nitrophenyl)butyric acid, 3-(4-methoxybenzoyl) propionic acid, 4-fluorophenoxyacetic acid, 2-(4-chlorophenoxy)propionic acid, 2-(4-chlorophenoxy)2-methylpropionic acid, (2,4-di-tert-pentylphenoxy)acetic acid, 2,6-difluorophenylacetic acid, 2,4-difluorophenylacetic acid, 2,5-difluorophenylacetic acid, 3,5-difluorophyenylacetic acid, 4-chloro-o-tolyloxyacetic acid, 2,3-dichlorophenoxyacetic acid, 2,6-dichlorophenylacetic acid, 2,4-dichlorophenylacetic acid, 2,4-dichlorophenoxyacetic acid, 3,4-dichlorophenylacetic acid, 3,4-dichlorophenoxyacetic acid, 3,5-bis(trifluoromethyl)phenylacetic acid, 4-(2,4-di-tert-pentylphenoxy)butyric acid, 2-(2,4-dichlorophenoxy) propionic acid, 4-(2,4-dichlorophenoxy) propionic acid, 2,4,5-trichlorophenoxyacetic acid, 2-(2,4,5-trichlorophenoxy) propionic acid, (3,4-dimethoxyphenyl)acetic acid, 4-benzyloxy-3-methoxyphenylacetic acid, 3,4-(methylenedioxy)phenylacetic acid, 5-methoxy-1-indanone-3-acetic acid, 3-(3,4-dimethoxyphenyl) propionic acid, 4-(3,4-dimethoxyphenyl)butyric acid, (2,5-dimethoxyphenyl) acetic acid, 2,4-dinitrophenylacetic acid, (3,5-dimethoxyphenyl)acetic acid, 3,4,5-trimethoxyphenylacetic acid, 3-(3,4,5-trimethoxyphenyl)propionic acid, 2,3,4,5,6-pentafluorophenylacetic acid, 4-biphenylacetic acid, 1-naphthylacetic acid, 2-naphthylacetic acid, o-trityl-2-naphthalenepropionic acid, (1-naphthoxy)acetic acid, (2-naphthoxy)acetic acid, 6-methoxy-α-methyl-2-naphthaleneacetic acid, 9-fluoreneacetic acid, 1-pyreneacetic acid, 1-pyrenebutyric acid, γ-oxo-1-pyrenebutyric acid, styrylacetic acid, cinnamic acid, α-methylcinnamic acid, α-fluorocinnamic acid, α-phenylcinnamic acid, 2-methylcinnamic acid, 2-fluorocinnamic acid, 2-(trifluoromethy)cinnamic acid, 2-chlorocinnamic acid, 2-methoxycinnamic acid, 2-nitrocinnamic acid, 3-fluorocinnamic acid, 3-(trifluoromethyl)cinnamic acid, 3-chlorocinnamic acid, 3-bromocinnamic acid, 3-methoxycinnamic acid, 3-nitrocinnamic acid, 4-methylcinnamic acid, 4-fluorocinnamic acid, 4-(trifluoromethyl)cinnamic acid, 4-chlorocinnamic acid, 4-bromocinnamic acid, 4-methoxycinnamic acid, 4-nitrocinnamic acid, 4-formylcinnamic acid, 2,6-difluorocinnamic acid, 2,4-difluorocinnamic acid, 2,5-difluorocinnamic acid, 3,4-difluorocinnamic acid, 3,5-difluorocinnamic acid, 2-chloro-6-fluorocinnamic acid, 2,4-dichlorocinnamic acid, 3,4-dichlorocinnamic acid, 5-bromo-2-methoxycinnamic acid, 2,3-dimethoxycinnamic acid, 2,4-dimethoxycinnamic acid, 2,5-dimethoxycinnamic acid, 3,4-dimethoxycinnamic acid, 3,4-(methylenedioxy)cinnamic acid, 3,5-dimethoxycinnamic acid, 2-chloro-5-nitrocinnamic acid, 4-chloro-3-nitrocinnamic acid, 2,3,4-trifluorocinnamic acid, 3,4,5-trimethoxycinnamic acid, 2,4,5-trimethoxycinnamic acid, α-methyl-2,4,5-trimethoxycinnamic acid, 4,5-dimethoxy-2-nitrocinnamic acid, 2,3,4,5,6-pentafluorocinnamic acid, 3-methylindene-2-carboxylic acid, 3-(4-methylbenzoyl)acrylic acid, 3-(2,5-dimethylbenzoyl)acrylic acid, 3-(2,3,5,6-tetramethylbenzoyl)acrylic acid, 3-(4-methoxybenzoyl) acrylic acid, 3-(4-ethoxybenzoyl)acrylic acid, 6-methylchromone-2-carboxylic acid, benzoic acid, o-toluic acid, 2-fluorobenzoic acid, α,α,α-trifluoro-o-toluic acid, 2-chlorobenzoic acid, 2-bromobenzoic acid, 2-iodobenzoic acid, o-anisic acid, 2-ethoxybenzoic acid, 2-nitrobenzoic acid, 2-acetylbenzoic acid, 2-(p-toluoyl)benzoic acid, m-toluic acid, 3-fluorobenzoic acid, α,α,α-trifluoro-m-toluic acid, 3-chlorobenzoic acid, 3-(chloromethyl) benzoic acid, 3-bromobenzoic acid, 3-iodobenzoic acid, m-anisic acid, 3-nitrobenzoic acid, 3-carboxybenzaldehyde, p-toluic acid, 4-ethylbenzoic acid, 4-n-propylbenzoic acid, 4-isopropylbenzoic acid, 4-n-butylbenzoic acid, 4-tert-butylbenzoic acid, 4-pentylbenzoic acid, 4-hexylbenzoic acid, 4-heptylbenzoic acid, 4-octylbenzoic acid, 4-vinylbenzoic acid, 4-fluorobenzoic acid, α,α,α-trifluoro-o-toluic acid, 4-chlorobenzoic acid, 4-bromobenzoic acid, 4-iodobenzoic acid, 4-(chloromethyl) benzoic acid, α-bromo-p-toluic acid, p-anisic acid, 4-(trifluoromethoxy) benzoic acid, 4-ethoxybenzoic acid, 4-n-propoxybenzoic acid, 4-butoxybenzoic acid, 4-pentyloxybenzoic acid, 4-hexyloxybenzoic acid, 4-heptyloxybenzoic acid, 4-octyloxybenzoic acid, 4-nonyloxybenzoic acid, 4-decyloxybenzoic acid, 4-nonyloxybenzoic acid, 4-dodecyloxybenzoic acid, 4-isopropoxybenzoic acid, 4-(2-cyclohexenyloxy)benzoic acid, 4-(methylthio)benzoic acid, 4-(ethylthio)benzoic acid, 4-nitrobenzoic acid, 4-acetylbenzoic acid, 4-carboxybenzaldehyde, 2,3-dimethylbenzoic acid, 2,6-dimethylbenzoic acid, 3-fluoro-2-methylbenzoic acid, 2,3-difluorobenzoic acid, 2,6-difluorobenzoic acid, 2-fluoro-6-(trifluoromethyl) benzoic acid, 2-fluoro-3-(trifluoromethyl)benzoic acid, 2,6-bis(trifluoromethyl)benzoic acid, 2-chloro-6-fluorobenzoic acid, 2-chloro-6-fluorophenylacetic acid, 2,3-dichlorobenzoic acid, 2,6-dichlorobenzoic acid, 2,3-dimethoxybenzoic acid, 2,6-dimethoxybenzoic acid, 2-methyl-6-nitrobenzoic acid, 3-methyl-2-nitrobenzoic acid, 2-methyl-3-nitrobenzoic acid, 3-chloro-2-nitrobenzoic acid, 2-chloro-3-nitrobenzoic acid, 2-bromo-3-nitrobenzoic acid, 3-methoxy-2-nitrobenzoic acid, 3,4-dimethylbenzoic acid, 2,4-dimethylbenzoic acid, 2,5-dimethylbenzoic acid, 5-fluoro-2-methylbenzoic acid, 3-fluoro-4-methylbenzoic acid, 2-fluoro-5-methylbenzoic acid, 3-bromo-4-methylbenzoic acid, 2,4-bis(trifluoromethyl)benzoic acid, 3-iodo-4-methylbenzoic acid, 2-chloro-5-(trifluoromethyl) benzoic acid, 2,5-bis(trifluoromethyl)benzoic acid, 2,4-difluorobenzoic acid, 3,4-difluorobenzoic acid, 4-fluoro-2-(trifluoromethyl)benzoic acid, 2-fluoro-4-(trifluoromethyl) benzoic acid, 2-chloro-4-fluorobenzoic acid, 3-chloro-4-fluorobenzoic acid, 2,4-dichlorobenzoic acid, 3,4-dichlorobenzoic acid, 2,5-difluorobenzoic acid, 2,5-dichlorobenzoic acid, 3-bromo-4-fluorobenzoic acid, 5-bromo-2-chlorobenzoic acid, 3-methoxy-4-methylbenzoic acid, 3-fluoro-4-methoxybenzoic acid, 4-chloro-o-anisic acid, 5-chloro-o-anisic acid, 2-bromo-5-methoxybenzoic acid, 2,4-dimethoxybenzoic acid, 2,5-dimethoxybenzoic acid, 3,4-dimethoxybenzoic acid, 3,4-diethoxybenzoic acid, piperonylic acid, 2-chloro-5-(methylthio)benzoic acid, 2-methoxy-4-(methylthio)benzoic acid, 5-methyl-2-nitrobenzoic acid, 4-methyl-3-nitrobenzoic acid, 3-methyl-4-nitrobenzoic acid, 2-nitro-α,α,α-trifluoro-p-toluic acid, 2-fluoro-5-nitrobenzoic acid, 4-chloro-2-nitrobenzoic acid, 2-chloro-4-nitrobenzoic acid, 4-fluoro-3-nitrobenzoic acid, 4-chloro-3-nitrobenzoic acid, 5-chloro-2-nitrobenzoic acid, 2-chloro-5-nitrobenzoic acid, 2-bromo-5-nitrobenzoic acid, 4-(bromomethyl)-3-nitrobenzoic acid, 2-methoxy-4-nitrobenzoic acid, 4-methoxy-3-nitrobenzoic acid, 3-methoxy-4-nitrobenzoic acid, 5-methoxy-2-nitrobenzoic acid, 2,4-dinitrobenzoic acid, 3,5-dimethylbenzoic acid, 3,5-di-tert-butylbenzoic acid, 3,5-difluorobenzoic acid, 3,5-bis(trifluoromethyl)benzoic acid, 3,5-dichlorobenzoic acid, 3,5-dibromobenzoic acid, 3-bromo-5-iodobenzoic acid, 3,5-dimethoxybenzoic acid, 3,5-dinitrobenzoic acid, 2,3,4-trifluorobenzoic acid, 2,3,6-trifluorobenzoic acid, 2,4,6-trimethylbenzoic acid, 2,4,6-trifluorobenzoic acid, 3,4,5-trifluorobenzoic acid, 2,4,6-trichlorobenzoic acid, 2,3,5-trichlorobenzoic acid, 2,3,5-triiodobenzoic acid, 2-bromo-4,5-dimethoxybenzoic acid, 3,4,5-trimethoxybenzoic acid, 3,4,5-triethoxybenzoic acid, 4,5-dimethoxy-2-nitrobenzoic acid, 3,5-dinitro-o-toluic acid, 3,5-dinitro-p-toluic acid, 2-chloro-3,5-dinitrobenzoic acid, 4-chloro-3,5-dinitrobenzoic acid, 2,5-dichloro-3-nitrobenzoic acid, 2,6-dichloro-3-nitrobenzoic acid, 2,3,4-trimethoxybenzoic acid, 2,4,5-trifluorobenzoic acid, 2-chloro-4,5-difluorobenzoic acid, 2,4-dichloro-5-fluorobenzoic acid, 2,4,5-trimethoxybenzoic acid, 2,3,4,5-tetrafluorobenzoic acid, 2,3,5,6-tetrafluorobenzoic acid, 2,4-dichloro-3,5-dinitrobenzoic acid, 2,3,5,6-tetrafluoro-p-toluic acid, 4-bromo-2,3,5,6-tetrafluorobenzoic acid, pentafluorobenzoic acid, 2-biphenylcarboxylic acid, 4'-(trifluoromethyl)-2-biphenylcarboxylic acid, 4-biphenylcarboxylic acid, 4'-ethyl-4-biphenylcarboxylic acid, 4'-octyloxy-4-biphenylcarboxylic acid, (x-phenyl-o-toluic acid, 2-bibenzylcarboxylic acid, 2,3,4,5,6-pentafluorophenoxyacetic acid, 2-phenoxybenzoic acid, 3-phenoxybenzoic acid, 2-benzoylbenzoic acid, 3-benzoylbenzoic acid, 4-benzoylbenzoic acid, 2-(4-fluorobenzoyl)benzoic acid, 2-(4-chlorobenzoyl)benzoic acid, 2-(4-chloro-3-nitrobenzoyl)benzoic acid, 1-naphthoic acid, 2-naphthoic acid, 4-fluoro-1-naphtnoic acid, 2-ethoxy-1-naphthoic acid, 1,8-naphthalaldehydic acid, 2-biphenylenecarboxylic acid, γ-oxo-5-acenaphthenebutyric acid, 9-fluorenecarboxylic acid, 1-fluorenecarboxylic acid, 4-fluorenecarboxylic acid, 9-fluorenone-1-carboxylic acid, 9-fluorenone-2-carboxylic acid, 9-fluorenone-4-carboxylic acid, 7-nitro-4-fluorenecarboxylic acid, chromone-2-carboxylic acid, 9-anthracenecarboxylic acid, anthraquinone-2-carboxylic acid, xanthene-9-carboxylic acid, 1-pyrenecarboxylic acid, UNICID 550, a long chain monoacid commercially available from Baker-Petrolite Corp., Cincinnati, Ohio, believed to be of the formula

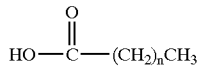

wherein n has an average value of about 36, UNICID 700, a long chain monoacid commercially available from Baker-Petrolite Corp., Cincinnati, Ohio, believed to be of the formula

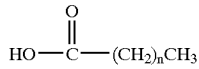

wherein n has an average value of about 46, and the like, as well as mixtures thereof.

The diisocyanate is of the general formula

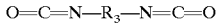

wherein $R_3$ is (i) an alkylene group (including linear, branched, saturated, unsaturated, cyclic, substituted, and unsubstituted alkylene groups, and wherein hetero atoms, such as oxygen, nitrogen, sulfur, silicon, phosphorus, and the like either may or may not be present in the alkylene group provided that no hetero atom is directly bonded to either of the isocyanate groups), in one embodiment with at least about 4 carbon atoms, in another embodiment with at least about 6 carbon atoms, and in yet another embodiment with at least about 8 carbon atoms, and in one embodiment with no more than about 200 carbon atoms, in another embodiment with no more than about 180 carbon atoms, and in yet another embodiment with no more than about 150 carbon atoms, although the number of carbon atoms can be outside of these ranges, (ii) an arylene group (including unsubstituted and substituted arylene groups, and wherein hetero atoms, such as oxygen, nitrogen, sulfur, silicon, phosphorus, and the like either may or may not be present in the arylene group provided that no hetero atom is directly bonded to either of the isocyanate groups), in one embodiment with at least about 6 carbon atoms, in another embodiment with at least about 10 carbon atoms, and in yet another embodiment with at least about 14 carbon atoms, and in one embodiment with no more than about 200 carbon atoms, in another embodiment with no more than about 180 carbon atoms, and in yet another embodiment with no more than about 150 carbon atoms, although the number of carbon atoms can be outside of these ranges, (iii) an arylalkylene group (including unsubstituted and substituted arylalkylene groups, wherein the alkyl portion of the arylalkylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkylene group provided that no hetero atom is directly bonded to either of the isocyanate groups), in one embodiment with at least about 7 carbon atoms, in another embodiment with at least about 8 carbon atoms, and in yet another embodiment with at least about 9 carbon atoms, and in one embodiment with no more than about 200 carbon atoms, in another embodiment with no more than about 180 carbon atoms, and in yet another embodiment with no more than about 160 carbon atoms, although the number of carbon atoms can be outside of these ranges, such as benzylene or the like, or (iv) an alkylarylene group (including unsubstituted and substituted alkylarylene groups, wherein the alkyl portion of the alkylarylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylarylene group provided that no hetero atom is directly bonded to either of the isocyanate groups), in one embodiment with at least about 7 carbon atoms, in another embodiment with at least about 8 carbon atoms, and in yet another embodiment with at least about 9 carbon atoms, and in one embodiment with no more than about 200 carbon atoms, in another embodiment with no more than about 180 carbon atoms, and in yet another embodiment with no more than about 160 carbon atoms, although the number of carbon atoms can be outside of these ranges, such as tolylene or the like, wherein the substituents on the substituted alkylene, arylene, arylalkylene, and alkylarylene groups can be (but are not limited to) halogen atoms, imine groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, nitro groups, nitroso groups, sulfone groups, acyl groups, azide groups, azo groups, cyanato groups, thiocyanato groups, carboxylate groups, urea groups, mixtures thereof, and the like, wherein two or more substituents can be joined together to form a ring.

Specific examples of suitable diisocyanates include 1,4-diisocyanatobutane, 1,6-diisocyanatohexane (HDI; commercially available from Aldrich Chemical Co., Milwaukee, Wis.), 1,8-diisocyanatooctane, 1,2-diisocyanatododecane, trimethylhexamethylene diisocyanate, 1,5-diisocyanato-2-methylpentane, cyclohexylene diisocyanate (including all isomers), bis(isocyanatomethane) cyclohexane (all isomers), 4,4'-methylenebis(cyclohexyl isocyanate), isophorone diisocyanate (IPDI; such as VESTANAT® IPDI, commercially available from Creanova Inc., Piscataway, N.H.), phenylene diisocyanate (all isomers), bis(isocyanatomethyl)benzene (all isomers), bis(1-isocyanato-1-methylethyl)benzene (all isomers), toluene diisocyanate (TDI) (all isomers), diphenylmethane-4,4'-diisocyanate (MDI), hydrogenated diphenylmethane-4,4'-diisocyanate (H12MDI), tetramethylxylene diisocyanate (TMXDI), naphthylene-1,5-diisocyanate, 3,3'-dimethoxy-4,4'-biphenyidiisocyanate, 3,3'-dimethyl-4,4'-bimethyl-4,4'-biphenyldiisocyanate, 4,4'-biphenyldiisocyanate, tetramethylene xylene diisocyanate, 4,4'-methylenebis(2,6-diethylphenyl isocyanate), 1-chloromethyl-2,4-diisocyanatobenzene, 4,4'-oxybis(phenyl isocyanate), DDI 1410, which is a dimer diisocyanate based on dimer acid, commercially available from Henkel Corporation, Kankakee, Ill., believed to be of the general formula

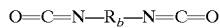

wherein $R_b$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10, and more specifically believed to include isomers of the formula

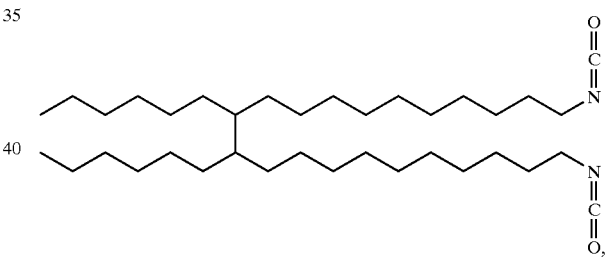

uretidione dimers of isocyanates, of the general formula

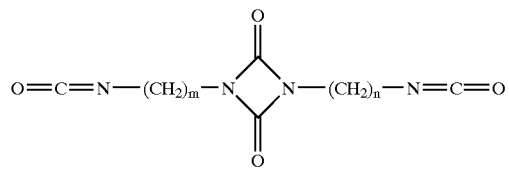

wherein m and n are each, independently of the others, integers representing the number of repeat —$CH_2$— units, such as the uretidione dimer of HDI, wherein m and n are each 6, commercially available as DESMODUR N100 from Bayer, and the like, as well as mixtures thereof.

When the tetra-amide prepared by the process disclosed herein is intended to be used in a phase change ink carrier or vehicle, in one specific embodiment the tetra-amide has a total number of carbon atoms of at least about 50, although the number of carbon atoms can be outside of this range.

While not being limited to any particular theory, the reaction is believed to proceed as follows:

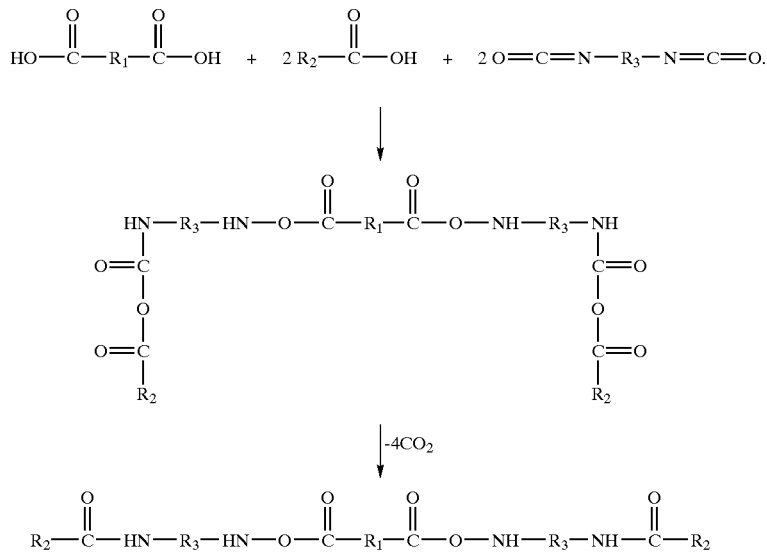

Typically, the diacid and the monoacid are first admixed and heated prior to addition of the diisocyanate reactant. The reaction can be carried out neat, with no need for a solvent; optionally, if desired, an anhydrous aprotic organic solvent can be used, such as xylene, sulfolane, or the like, as well as mixtures thereof, in any desired or effective amount, in one embodiment about 2 parts by weight solvent per every one part by weight reactants, although the relative amounts can be outside of this range.

In one specific embodiment, a solvent that is solid at room temperature can also be employed, such as a polyethylene wax or the like; such a material can facilitate interaction between the acids and the diisocyanate to promote quick and complete reaction and can reduce the viscosity of the reaction mixture while also being a useful ink ingredient when the resulting tetra-amide product is used in a phase change ink. In this embodiment, the solid solvent can be present in any desired or effective amount. Since the solid solvent and the tetra-amide product are generally not separated subsequent to completion of the reaction, the solid solvent is generally not present in an amount greater than the amount of said solvent that is desired in the ink composition. There are no lower limits on the amount of solid solvent. In one specific embodiment, the solid solvent and the reactants are present in about a 1:1 ratio by weight, although the relative amounts can be outside of this range.

The diacid and monoacid, if either of them are solid at room temperature, can be heated to any desired or effective temperature to enable them to melt and be admixed, in one embodiment at least about 80° C., in another embodiment at least about 100IC, and in yet another embodiment at least about 120° C., and in one embodiment no more than about 300° C., in another embodiment no more than about 280° C., and in yet another embodiment no more than about 220° C., although the temperature can be outside of these ranges.

The monoacid and the diacid are heated and admixed for any desired or effective period of time to enable good mixing of the ingredients, in one embodiment at least about 1 minute, in another embodiment at least about 3 minutes, and in yet another embodiment at least about 5 minutes, and in one embodiment no more than about 60 minutes, in another embodiment no more than about 50 minutes, and in yet another embodiment no more than about 40 minutes, although the time can be outside of these ranges.

While not required, in one specific embodiment, the reaction takes place in an inert atmosphere, such as nitrogen, argon, or the like, to minimize discoloration of the tetra-amide product that might be caused by oxidation.

Since gaseous carbon dioxide is a reaction product, in one specific embodiment, the reaction takes place at atmospheric pressure or lower, although the pressure can also be higher than atmospheric pressure if so desired.

Thereafter, the diisocyanate is added to the mixture of monoacid and diacid. The reaction mixture thus formed is then heated to any desired or effective temperature, in one embodiment at least about 60° C., in another embodiment at least about 80° C., and in yet another embodiment at least about 120° C., and in one embodiment no more than about 400° C., in another embodiment no more than about 350° C., in yet another embodiment no more than about 300° C., and in still another embodiment no more than about 200° C., although the temperature can be outside of these ranges.

The monoacid, the diacid, and the diisocyanate are heated and admixed for any desired or effective period of time, in one embodiment at least about 10 minutes, in another embodiment at least about 30 minutes, and in yet another embodiment at least about 60 minutes, and in one embodiment no more than about 20 hours, in another embodiment no more than about 15 hours, and in yet another embodiment no more than about 13 hours, although the time can be outside of these ranges. If desired, stepwise heating can be employed to maintain a smooth reaction, or to avoid vigorous bubbling as a result of generated $CO_2$, with a relatively lower temperature selected at the beginning of the reaction, followed by a relatively higher temperature selected later in the course of the reaction to complete the reaction; increased temperatures later in the reaction process can be particularly helpful to drive the reaction to completion when no catalyst is employed.

The reactants are admixed in any desired or effective amounts. The relative amounts of monoacid and diacid can be in one embodiment at least about 1 mole of monoacid per every one mole of diacid, in another embodiment at least about 2 moles of monoacid per every one mole of diacid, and in yet another embodiment at least about 2.5 moles of monoacid per every one mole of diacid, and in one embodiment no more than about 10 moles of monoacid per every one mole of diacid, in another embodiment no more than about 8 moles of monoacid per every one mole of diacid, and in yet another embodiment no more than about 6 moles of monoacid per every one mole of diacid, although the relative amounts can be outside of these ranges.

The relative amounts of diisocyanate and diacid can be in one embodiment at least about 0.5 mole of diisocyanate per every one mole of diacid, in another embodiment at least about 0.7 mole of diisocyanate per every one mole of diacid, and in yet another embodiment at least about 0.9 mole of diisocyanate per every one mole of diacid, and in one embodiment no more than about 10 moles of diisocyanate per every one mole of diacid, in another embodiment no more than about 8 moles of diisocyanate per every one mole of diacid, and in yet another embodiment no more than about 6 moles of diisocyanate per every one mole of diacid, although the relative amounts can be outside of these ranges.

When it is desired to minimize or eliminate residual isocyanate groups in the product, the ratio of total number of COOH groups to total number of NCO groups is in one embodiment at least about 1:1, in another embodiment at least about 1.03:1, and in yet another embodiment at least about 1.05:1, and in one embodiment no more than about 10:1, in another embodiment no more than about 7:1, and in yet another embodiment no more than about 5:1, although the ratio of total COOH groups to NCO groups can be outside of these ranges.

Optionally, a catalyst can be used in the reaction. When used, the catalyst can be added at any stage in the reaction process, such as adding it to the mixture of acids, adding it with the isocyanate, adding it after addition of the isocyanate, or the like. Catalysts can be helpful for purposes such as reducing the amount of time required for completion of the reaction, increasing product yields, driving the reaction to completion to minimize or eliminate residual NCO groups, or the like. Examples of suitable catalysts include (but are not limited to) tertiary amines, such as triethyl amine and the like, basic compounds, such as potassium acetate and the like, anhydrous hydrogen halides and hydrolytically unstable halide compounds, such as dibutyltin dichloride and the like, alkali metal salts of alcohols, such as sodium methoxide, potassium octoxide, and the like, 1-oxide, 1-sulfide, and 1-hydrocarbylimino derivatives of phospholenes, phospholanes, and phosphetanes, such as 1,3-dimethyl-2-phospholene-oxide and the like, zinc acid salts, such as ZINC HEX-CEM, a zinc carboxylate salt of 2-ethylhexanoic acid, commercially available from OMG Americas, Inc., Westlake, Ohio, and the like, as well as mixtures thereof.

When present, the optional catalyst is present in any desired or effective amount, in one embodiment at least about 0.0001 mole of catalyst per every one mole of diacid, in another embodiment at least about 0.0005 mole of catalyst per every one mole of diacid, and in yet another embodiment at least about 0.001 mole of catalyst per every one mole of diacid, and in one embodiment no more than about 10 moles of catalyst per every one mole of diacid, in another embodiment no more than about 5 moles of catalyst per every one mole of diacid, and in yet another embodiment no more than about 3 moles of catalyst per every one mole of diacid, although the relative amounts can be outside of these ranges.

The methods disclosed herein for preparing tetra-amides are desirable in that they can be carried out at relatively low temperatures, in some embodiments of 200° C. or lower. In addition, the synthetic methods disclosed herein generate environmentally innocuous carbon dioxide as a byproduct, and no volatile or low-boiling toxic amines are released.

The tetra-amide can, if desired, function as the sole ink carrier. Optionally, the tetra-amide can be admixed with other materials to create an ink carrier. Any desired or effective carrier composition can be used. Examples of suitable ink carrier materials include fatty amides, such as monoamides and the like. Further information on fatty amide carrier materials is disclosed in, for example, U.S. Pat. No. 4,889,560, U.S. Pat. No. 4,889,761, U.S. Pat. No. 5,194,638, U.S. Pat. No. 4,830,671, U.S. Pat. No. 6,174,937, U.S. Pat. No. 5,372,852, U.S. Pat. No. 5,597,856, U.S. Pat. No. 6,174,937, and British Patent GB 2 238 792, the disclosures of each of which are totally incorporated herein by reference.

Also suitable as phase change ink carrier materials are isocyanate-derived resins and waxes, such as urethane isocyanate-derived materials, urea isocyanate-derived materials, urethane/urea isocyanate-derived materials, mixtures thereof, and the like. Further information on isocyanate-derived carrier materials is disclosed in, for example, U.S. Pat. No. 5,750,604, U.S. Pat. No. 5,780,528, U.S. Pat. No. 5,782,966, U.S. Pat. No. 5,783,658, U.S. Pat. No. 5,827,918, U.S. Pat. No. 5,830,942, U.S. Pat. No. 5,919,839, U.S. Pat. No. 6,255,432, U.S. Pat. No. 6,309,453, British Patent GB 2 294 939, British Patent GB 2 305 928, British Patent GB 2 305 670, British Patent GB 2 290 793, PCT Publication WO 94/14902, PCT Publication WO 97/12003, PCT Publication WO 97/13816, PCT Publication WO 96/14364, PCT Publication WO 97/33943, and PCT Publication W095/04760, the disclosures of each of which are totally incorporated herein by reference.

Mixtures of fatty amide materials and isocyanate-derived materials can also be employed in the ink carrier composition.

Additional suitable phase change ink carrier materials include paraffins, microcrystalline waxes, polyethylene waxes, ester waxes, amide waxes, fatty acids, fatty alcohols, fatty amides and other waxy materials, sulfonamide materials, resinous materials made from different natural sources (such as, for example, tall oil rosins and rosin esters), and many synthetic resins, oligomers, polymers and copolymers, such as ethylene/vinyl acetate copolymers, ethylene/acrylic acid copolymers, ethylene/vinyl acetate/acrylic acid copolymers, copolymers of acrylic acid with polyamides, and the like, ionomers, and the like, as well as mixtures thereof. One or more of these materials can also be employed in a mixture with a fatty amide material and/or an isocyanate-derived material.

In one specific embodiment, the phase change ink carrier comprises (a) a polyethylene wax, present in the ink in an amount in one embodiment of at least about 25 percent by weight of the ink, in another embodiment of at least about 30 percent by weight of the ink, and in yet another embodiment of at least about 37 percent by weight of the ink, and in one embodiment of no more than about 60 percent by weight of the ink, in another embodiment of no more than about 53 percent by weight of the ink, and in yet another embodiment of no more than about 48 percent by weight of the ink, although the amount can be outside of these ranges; (b) a stearyl stearamide wax, present in the ink in an amount in one embodiment of at least about 8 percent by weight of the ink, in another embodiment of at least about 10 percent by weight of the ink, and in yet another embodiment of at least about 12 percent by weight of the ink, and in one embodiment of no more than about 32 percent by weight of the ink, in another embodiment of no more than about 28 percent by weight of the ink, and in yet another embodiment of no more than about 25 percent by weight of the ink, although the amount can be outside of these ranges; (c) a tetra-amide prepared according to the present invention that is the reaction product of dimer acid, a diisocyanate, and a long chain hydrocarbon having greater than thirty six carbon atoms and having a terminal carboxylic acid group, present in the ink in an amount in one embodiment of at least about 10 percent by weight of the ink, in another embodiment of at least about 13 percent by weight of the ink, and in yet another embodiment of at least about 16 percent by weight of the ink, and in one embodiment of no more than about 32 percent by weight of the ink, in another embodiment of no more than about 27 percent by weight of the ink, and in yet another embodiment of no more than about 22 percent by weight of the ink, although the amount can be outside of these ranges; (d) a urethane resin derived from the reaction of two equivalents of hydroabietyl alcohol and one equivalent of isophorone diisocyanate, present in the ink in an amount in one embodiment of at least about 6 percent by weight of the ink, in another embodiment of at least about 8 percent by weight of the ink, and in yet another embodiment of at least about 10 percent by weight of the ink, and in one embodiment of no more than about 16 percent by weight of the ink, in another embodiment of no more than about 14 percent by weight of the ink, and in yet another embodiment of no more than about 12 percent by weight of the ink, although the amount can be outside of these ranges; (e) a urethane resin that is the adduct of three equivalents of stearyl isocyanate and a glycerol-based alcohol, present in the ink in an amount in one embodiment of at least about 2 percent by weight of the ink, in another embodiment of at least about 3 percent by weight of the ink, and in yet another embodiment of at least about 4.5 percent by weight of the ink, and in one embodiment of no more than about 13 percent by weight of the ink, in another embodiment of no more than about 10 percent by weight of the ink, and in yet another embodiment of no more than about 7.5 percent by weight of the ink, although the amount can be outside of these ranges; and (f) an antioxidant, present in the ink in an amount in one embodiment of at least about 0.01 percent by weight of the ink, in another embodiment of at least about 0.05 percent by weight of the ink, and in yet another embodiment of at least about 0.1 percent by weight of the ink, and in one embodiment of no more than about 1 percent by weight of the ink, in another embodiment of no more than about 0.5 percent by weight of the ink, and in yet another embodiment of no more than about 0.3 percent by weight of the ink, although the amount can be outside of these ranges.

The ink carrier is present in the phase change ink in any desired or effective amount, in one embodiment of at least about 0.1 percent by weight of the ink, in another embodiment of at least about 50 percent by weight of the ink, and in yet another embodiment of at least about 90 percent by weight of the ink, and in one embodiment of no more than about 99 percent by weight of the ink, in another embodiment of no more than about 98 percent by weight of the ink, and in yet another embodiment of no more than about 95 percent by weight of the ink, although the amount can be outside of these ranges.

The phase change ink compositions also contain a colorant. Any desired or effective colorant can be employed, including dyes, pigments, mixtures thereof, and the like, provided that the colorant can be dissolved or dispersed in the ink vehicle. The phase change carrier compositions can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba-Geigy); Direct Brilliant Pink B (Crompton & Knowles); Aizen Spilon Red C-BH (Hodogaya Chemical); Kayanol Red 3BL (Nippon Kayaku); Levanol Brilliant Red 3BW (Mobay Chemical); Levaderm Lemon Yellow (Mobay Chemical); Spirit Fast Yellow 3G; Aizen Spilon Yellow C-GNH (Hodogaya Chemical); Sirius Supra Yellow GD 167; Cartasol Brilliant Yellow 4GF (Sandoz); Pergasol Yellow CGP (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc. A (Morton-Thiokol); Diaazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 26050] (BASF), Intratherm Yellow 346 from Crompton and Knowles, C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are totally incorporated herein by reference, and commercially available from, for example, Milliken & Company as Milliken Ink Yellow 12, Milliken Ink Blue 92, Milliken Ink Red 357, Milliken Ink Yellow 1800, Milliken Ink Black 8915–67, uncut Reactant Orange X-38, uncut Reactant Blue X-17, Solvent Yellow 162, Acid Red 52, Solvent Blue 44, and uncut Reactant Violet X-80.

Pigments are also suitable colorants for the phase change inks. Examples of suitable pigments include Violet Toner VT-8015 (Paul Uhlich); Paliogen Violet 5100 (BASF); Paliogen Violet 5890 (BASF); Permanent Violet VT 2645 (Paul Uhlich); Heliogen Green L8730 (BASF); Argyle Green XP-111-S (Paul Uhlich); Brilliant Green Toner GR 0991 (Paul Uhlich); Lithol Scarlet D3700 (BASF); Toluidine Red (Aldrich); Scarlet for Thermoplast NSD PS PA (Ugine Kuhlmann of Canada); E.D. Toluidine Red (Aldrich); Lithol Rubine Toner (Paul Uhlich); Lithol Scarlet 4440 (BASF); Bon Red C (Dominion Color Company); Royal Brilliant Red RD-8192 (Paul Uhlich); Oracet Pink RF (Ciba-Geigy); Paliogen Red 3871K (BASF); Paliogen Red 3340 (BASF); Lithol Fast Scarlet L4300 (BASF); Heliogen Blue L6900, L7020 (BASF); Heliogen Blue K6902, K6910 (BASF); Heliogen Blue D6840, D7080 (BASF); Sudan Blue OS (BASF); Neopen Blue FF4012 (BASF); PV Fast Blue B2G01 (American Hoechst); Irgalite Blue BCA (Ciba-Geigy); Paliogen Blue 6470 (BASF); Sudan III (Red Orange) (Matheson, Colemen Bell); Sudan II (Orange) (Matheson, Colemen Bell); Sudan Orange G (Aldrich), Sudan Orange 220 (BASF); Paliogen Orange 3040 (BASF); Ortho Orange OR 2673 (Paul Uhlich); Paliogen Yellow 152, 1560 (BASF); Lithol Fast Yellow 0991K (BASF); Paliotol Yellow 1840 (BASF); Novoperm Yellow FGL (Hoechst); Permanent Yellow YE 0305 (Paul Uhlich); Lumogen Yellow D0790 (BASF); Suco-Yellow L1250 (BASF); Suco-Yellow D1355 (BASF); Suco Fast Yellow D1355, D1351 (BASF); Hostaperm Pink E (American Hoechst); Fanal Pink D4830 (BASF); Cinquasia Magenta (Du Pont); Paliogen Black L0084 (BASF); Pigment Black K801 (BASF); and carbon blacks such as REGAL 330® (Cabot), Carbon Black 5250, Carbon Black 5750 (Columbia Chemical), and the like.

Also suitable are the colorants disclosed in U.S. Pat. No. 6,472,523, Copending application U.S. Ser. No. 10/072,210, Feb. 8, 2002, entitled "Ink Compositions Containing Phthalocyanines," U.S. Pat. No. 6,476,219, U.S. Pat. No. 6,576,747, Copending application U.S. Ser. No. 10/185,994, filed Jun. 27, 2002, entitled "Dimeric Azo Pyridone Colorants," Copending application U.S. Ser. No. 10/184,269, filed Jun. 27, 2002, entitled "Phase Change Inks Containing Dimeric Azo Pyridone Colorants," Copending application U.S. Ser. No. 10/185,264, filed Jun. 27, 2002, entitled "Phase Change Inks Containing Azo Pyridone Colorants," U.S. Pat. No. 6,590,082, Copending application U.S. Ser. No. 10/185,597, filed Jun. 27, 2002, entitled "Process for Preparing Substituted Pyridone Compounds," U.S. Pat. No. 6,576,748, Copending application U.S. Ser. No. 10/186,023, filed Jun. 27, 2002, entitled "Dimeric Azo Pyridone Colorants," Copending application U.S. Ser. No. 10/184,266, filed Jun. 27, 2002, entitled "Phase Change Inks Containing Dimeric Azo Pyridone Colorants," Copending application U.S. Ser. No. 10/260,146, filed Sep. 27, 2002, entitled "Colorant Compounds," and Copending application U.S. Ser. No. 10/260,379, filed Sep. 27, 2002, entitled "Methods for Making Colorant Compounds," the disclosures of each of which are totally incorporated herein by reference.

Other ink colors besides the subtractive primary colors can be desirable for applications such as postal marking, industrial marking, and labelling using phase change printing, and the inks are applicable to these needs. Further, infrared (IR) or ultraviolet (UV) absorbing dyes can also be incorporated into the inks for use in applications such as "invisible" coding or marking of products. Examples of such infrared and ultraviolet absorbing dyes are disclosed in, for example, U.S. Pat. No. 5,378,574, U.S. Pat. No. 5,146,087, U.S. Pat. No. 5,145,518, U.S. Pat. No. 5,543,177, U.S. Pat. No. 5,225,900, U.S. Pat. No. 5,301,044, U.S. Pat. No. 5,286,286, U.S. Pat. No. 5,275,647, U.S. Pat. No. 5,208,630, U.S. Pat. No. 5,202,265, U.S. Pat. No. 5,271,764, U.S. Pat. No. 5,256,193, U.S. Pat. No. 5,385,803, and U.S. Pat. No. 5,554,480, the disclosures of each of which are totally incorporated herein by reference.

In a specific embodiment, the colorant is an isocyanate-derived colored resin as disclosed in, for example, U.S. Pat. No. 5,780,528 and U.S. Pat. No. 5,919,839, the disclosures of each of which are totally incorporated herein by reference. In this embodiment, the colorant is the reaction product of a hydroxyl-substituted or primary or secondary amino-substituted chromophore with an isocyanate. Examples of suitable isocyanates include monoisocyanates, diisocyanates, triisocyanates, copolymers of a diisocyanate, copolymers of a triisocyanate, polyisocyanates (having more than three isocyanate functional groups), and the like, as well as mixtures thereof. Specific examples of suitable isocyanates include those listed hereinabove as being suitable for reaction with the hydroxyl-substituted or amino-substituted antioxidant. Examples of suitable hydroxyl-substituted and primary or secondary amino-substituted chromophores include those disclosed in, for example, U.S. Pat. No. 3,157,633, U.S. Pat. No. 3,927,044, U.S. Pat. No. 3,994,835, U.S. Pat. No. 4,102,644, U.S. Pat. No. 4,113,721, U.S. Pat. No. 4,132,840, U.S. Pat. No. 4,137,243, U.S. Pat. No. 4,170,564, U.S. Pat. No. 4,284,729, U.S. Pat. No. 4,507,407, U.S. Pat. No. 4,640,690, U.S. Pat. No. 4,732,570, U.S. Pat. No. 4,751,254, U.S. Pat. No. 4,751,254, U.S. Pat. No. 4,761,502, U.S. Pat. No. 4,775,748, U.S. Pat. No. 4,812,141, U.S. Pat. No. 4,846,846, U.S. Pat. No. 4,871,371, U.S. Pat. No. 4,912,203, U.S. Pat. No. 4,978,362, U.S. Pat. No. 5,043,013, U.S. Pat. No. 5,059,244, U.S. Pat. No. 5,149,800, U.S. Pat. No. 5,177,200, U.S. Pat. No. 5,270,363, U.S. Pat. No. 5,290,921, and U.S. Pat. No. 5,731,398, the disclosures of each of which are totally incorporated herein by reference. Hydroxyl-containing and primary or secondary amino-containing colorants from the classes of Color Index (C.I.) Solvent Dyes, Disperse Dyes, modified Acid and Direct Dyes, Basic Dyes, Sulphur Dyes, Vat Dyes, and the like can also be used.

The colorant is present in the phase change ink in any desired or effective amount to obtain the desired color or hue, typically at least about 0.1 percent by weight of the ink, preferably at least about 0.2 percent by weight of the ink, and more preferably at least about 0.5 percent by weight of the ink, and typically no more than about 50 percent by weight of the ink, preferably no more than about 20 percent by weight of the ink, and more preferably no more than about 10 percent by weight of the ink, although the amount can be outside of these ranges.

The inks can also optionally contain an antioxidant. The optional antioxidants of the ink compositions protect the images from oxidation and also protect the ink components from oxidation during the heating portion of the ink preparation process. Specific examples of suitable antioxidants include NAUGUARD® 524, NAUGUARD® 76, and NAUGUARD® 512, commercially available from Uniroyal Chemical Company, Oxford, Conn., IRGANOX® 1010, commercially available from Ciba Geigy, and the like. When present, the optional antioxidant is present in the ink in any desired or effective amount, in one embodiment of at least about 0.01 percent by weight of the ink, in another embodiment of at least about 0.1 percent by weight of the ink, and in yet another embodiment of at least about 1 percent by weight of the ink, and in one embodiment of no more than about 20 percent by weight of the ink, in another embodiment of no more than about 5 percent by weight of the ink, and in yet another embodiment of no more than about 3 percent by weight of the ink, although the amount can be outside of these ranges.

The inks can also optionally contain a viscosity modifier. Examples of suitable viscosity modifiers include aliphatic ketones, such as stearone, and the like. When present, the optional viscosity modifier is present in the ink in any desired or effective amount, in one embodiment of at least about 0.1 percent by weight of the ink, in another embodiment of at least about 1 percent by weight of the ink, and in yet another embodiment of at least about 10 percent by weight of the ink, and in one embodiment of no more than about 99 percent by weight of the ink, in another embodiment of no more than about 30 percent by weight of the ink, and in yet another embodiment of no more than about 15 percent by weight of the ink, although the amount can be outside of these ranges.

Other optional additives to the inks include clarifiers, such as UNION CAMP® X37-523-235 (commercially available from Union Camp), in an amount in one embodiment of at least about 0.01 percent by weight of the ink, in another embodiment of at least about 0.1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, tackifiers, such as FORAL® 85, a glycerol ester of hydrogenated abietic (rosin) acid (commercially available from Hercules), FORAL® 105, a pentaerythritol ester of hydroabietic (rosin) acid (commercially available from Hercules), CELLOLYN® 21, a hydroabietic (rosin) alcohol ester of phthalic acid (commercially available from Hercules), ARAKAWA KE-311 Resin, a triglyceride of hydrogenated abietic (rosin) acid (commercially available from Arakawa Chemical Industries, Ltd.), synthetic polyterpene resins such as NEVTAC® 2300, NEVTAC® 100, and NEVTACO 80 (commercially available from Neville Chemical Company), WINGTACK® 86, a modified synthetic polyterpene resin (commercially available from Goodyear), and the like, in an amount in one embodiment of at least about 0.1 percent by weight of the ink, in another embodiment of at least about 5 percent by weight of the ink, and in yet another embodiment of at least about 10 percent by weight of the ink, and in one embodiment of no more than about 98 percent by weight of the ink, in another embodiment of no more than about 75 percent by weight of the ink, and in yet another embodiment of no more than about 50 percent by weight of the ink, although the amount can be outside of these range, adhesives, such as VERSAMID® 757, 759, or 744 (commercially available from Henkel), in an amount in one embodiment of at least about 0.1 percent by weight of the ink, in another embodiment of at least about 1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, plasticizers, such as UNIPLEX® 250 (commercially available from Uniplex), the phthalate ester plasticizers commercially available from Monsanto under the trade name SANTICIZER®, such as dioctyl phthalate, diundecyl phthalate, alkylbenzyl phthalate (SANTICIZER® 278), triphenyl phosphate (commercially available from Monsanto), KP-140®, a tributoxyethyl phosphate (commercially available from FMC Corporation), MORFLEX® 150, a dicyclohexyl phthalate (commercially available from Morflex Chemical Company Inc.), trioctyl trimellitate (commercially available from Eastman Kodak Co.), and the like, in an amount in one embodiment of at least about 0.1 percent by weight of the ink, in another embodiment of at least about 1 percent by weight of the ink, and in yet another embodiment of at least about 2 percent by weight of the ink, and in one embodiment of no more than about 50 percent by weight of the ink, in another embodiment of no more than about 30 percent by weight of the ink, and in yet another embodiment of no more than about 10 percent by weight of the ink, although the amount can be outside of these ranges, and the like.

The inks can also optionally contain other materials. The phase change carrier composition is typically designed for use in either a direct printing mode or an indirect or offset printing transfer system.

In the direct printing mode, the phase change carrier composition in specific embodiments contains one or more materials that enable the phase change ink (1) to be applied in a thin film of uniform thickness on the final recording substrate (such as paper, transparency material, or the like) when cooled to ambient temperature after printing directly to the recording substrate, (2) to be ductile while retaining sufficient flexibility so that the applied image on the substrate will not fracture upon bending, and (3) to possess a high degree of lightness, chroma, transparency, and thermal stability.

In an offset printing transfer or indirect printing mode, the phase change carrier composition in specific embodiments exhibits not only the characteristics desirable for direct printing mode inks, but also certain fluidic and mechanical properties desirable for use in such a system, as described in, for example, U.S. Pat. No. 5,389,958 the disclosure of which is totally incorporated herein by reference.

The ink compositions typically have melting points no lower than about 50° C., preferably no lower than about 70° C., and more preferably no lower than about 80° C., and typically have melting points no higher than about 160° C., preferably no higher than about 140° C., and more preferably no higher than about 100° C., although the melting point can be outside of these ranges.

The ink compositions generally have melt viscosities at the jetting temperature (typically no lower than about 75° C., preferably no lower than about 100° C., and more preferably no lower than about 120° C., and typically no higher than about 180° C., preferably no higher than about 150° C., and more preferably no higher than about 130° C., although the jetting temperature can be outside of these ranges) typically of no more than about 30 centipoise, preferably no more than about 20 centipoise, and even more preferably no more than about 15 centipoise, and typically of no less than about 2 centipoise, preferably no less than about 5 centipoise, and even more preferably no less than about 7 centipoise, although the melt viscosity can be outside of these ranges. Since image hardness tend to drop with lower viscosities, it is preferred that the viscosity be as low as possible while still retaining the desired degree of image hardness.

The ink compositions can be prepared by any desired or suitable method. For example, the ink ingredients can be mixed together, followed by heating, typically to a temperature of from about 100 to about 140° C., although the temperature can be outside of this range, and stirring until a homogeneous ink composition is obtained, followed by cooling the ink to ambient temperature (typically from about 20 to about 25° C.). The inks are solid at ambient temperature.

The inks can be employed in apparatus for direct printing ink jet processes and in indirect (offset) printing ink jet applications. Another embodiment is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. An offset or indirect printing process is also disclosed in, for example, U.S. Pat. No. 5,389,958, the disclosure of which is totally incorporated herein by reference. In one specific embodiment of the offset or indirect printing process, the intermediate transfer member is heated to a temperature above that of the final recording sheet and below that of the melted ink in the printing apparatus. In one specific embodiment, the printing apparatus employs a piezoelectric printing process wherein droplets of the ink are caused to be ejected in imagewise pattern by oscillations of piezoelectric vibrating elements. The inks can also be employed in other hot melt printing processes, such as hot melt acoustic ink jet printing, hot melt thermal ink jet printing, hot melt continuous stream or deflection ink jet printing, or the like. Phase change inks can also be used in printing processes other than hot melt ink jet printing processes, such as hot melt gravure printing, hot melt medical imaging printing, or the like.

Any suitable substrate or recording sheet can be employed, including plain papers such as XEROX® 4024 papers, XEROX® Image Series papers, Courtland 4024 DP paper, ruled notebook paper, bond paper, silica coated papers such as Sharp Company silica coated paper, JuJo paper, and the like, transparency materials, fabrics, textile products, plastics, polymeric films, inorganic substrates such as metals and wood, and the like.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

To a 1,000 milliliter four-neck roundbottom flask fitted with a TRUBORE stirrer, $N_2$ inlet and outlet, and thermocouple-temperature controller was added 86.3 grams (0.150 moles) of PRIPOL 1006 (dimer acid, obtained from Uniqema, Chicago, Ill.), believed to be of the general formula

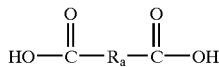

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; more specifically, the dimer acid is believed to include isomers of the formula

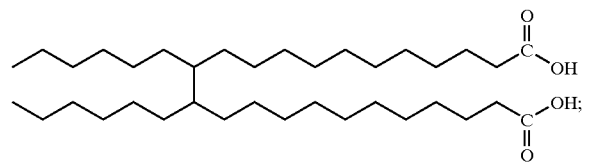

and 275.6 grams (0.306 moles) of UNICID 700 (long chain monoacid, obtained from Baker-Petrolite Corp., Cincinnati, Ohio), believed to be of the formula

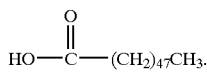

The mixture was heated to 115° C. and stirred at atmospheric pressure under $N_2$. 66.9 grams (0.300 moles) of VESTANAT® IPDI (isophorone diisocyanate, obtained from Creanova Inc., Piscataway, N.H.), of the formula

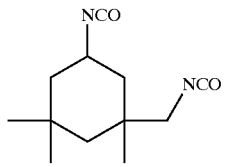

was added to the reaction mixture. An exotherm to 127° C. and evolution of gas from the reaction mixture were observed. The reaction temperature was then increased to 150° C. and maintained at that temperature for 1 hour; thereafter the temperature was raised to 180° C. and maintained at that temperature for 1.5 hours; thereafter the temperature was raised to 200° C. and maintained at that temperature for 1 hour. The Fourier Transform Infrared Spectroscopy (FT-IR) was run on a PERKIN ELMER 16 C FT-IR during the reaction to ensure that all of the isocyante (NCO) was consumed and that the amide moiety was formed. The absence (disappearance) of a peak around 2285 $cm^{-1}$ corresponding to the isocyanate group (NCO) and the appearance of a peak around 1650 $cm^{-1}$ corresponding to the amide group (CONH) were used to confirm progress of the reaction. The final product was a translucent solid resin at room temperature having the following properties: acid number 2.3; viscosity at 135° C. 103.4 centipoise (as measured by a Ferranti-Shirley cone-plate viscometer); melting points 98.3° C. and 105.9° C. (as measured by differential scanning calorimetery using a DUPONT 2100 calorimeter at a scan rate of 20° C. per minute). It is believed that a major product of the reaction fin addition to minor amounts of diamide products) was a tetra-amide of the formula

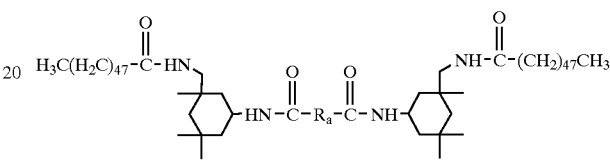

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; at least some isomers of the tetra-amide product were believed to be of the formula

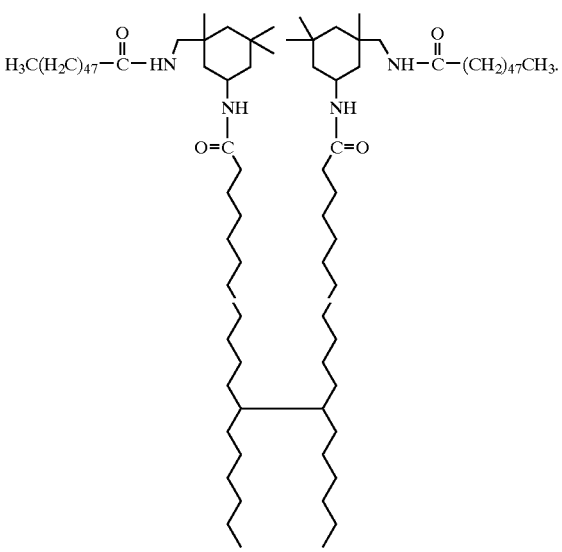

EXAMPLE II

The process of Example I was repeated except that 1,6-diisocyanatohexane (98%, obtained from Aldrich Chemical Company, Milwaukee, Wis.), of the formula

was used instead of the isophorone diisocyanate. The final product was a translucent solid resin at room temperature having the following properties: acid number 4.1; viscosity at 135° C. 115.1 centipoise (as measured by a Ferranti-Shirley cone-plate viscometer). It is believed that a major product of the reaction (in addition to minor amounts of diamide products) was a tetra-amide of the formula

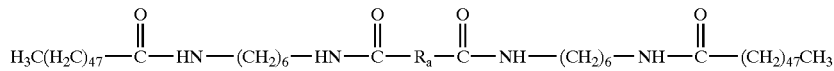

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; at least some isomers of the tetra-amide product were believed to be of the formula

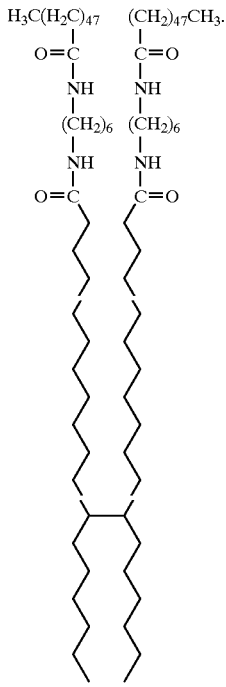

EXAMPLE III

The process of Example I was repeated except that the reaction temperature was increased to 150° C. and maintained at that temperature for 6 hours after the addition of isophorone diisocyanate. FT-IR spectra of the final product showed disappearance of the NCO peak around 2285 cm$^{-1}$ and the appearance of an amide peak around 1650 cm$^{-1}$. The final product was a translucent solid resin at room temperature having the following properties: acid number 5.1; viscosity at 135° C. 101.1 centipoise (as measured by a Ferranti-Shirley cone-plate viscometer); melting points 99.4° C. and 105.5° C. (as measured by differential scanning calorimetery using a DUPONT 2100 calorimeter at a scan rate of 20° C. per minute). It is believed that a major product of the reaction (in addition to minor amounts of diamide products) was a tetra-amide of the formula

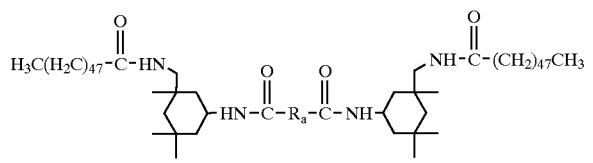

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; at least some isomers of the tetra-amide product were believed to be of the formula

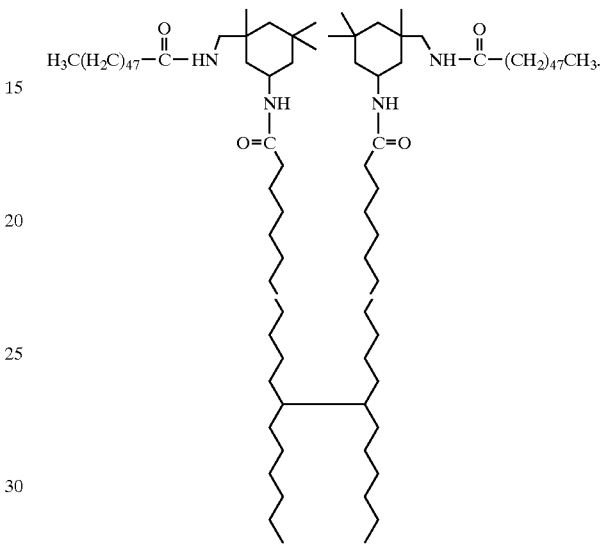

EXAMPLE IV

To a 1,000 milliliter four-neck roundbottom flask fitted with a TRUBORE stirrer, N$_2$ inlet and outlet, and thermocouple-temperature controller was added 85.9.grams (0.150 moles) of PRIPOL 1006, 279.0 grams (0.312 moles) of UNICID 700, and 2.03 grams of "22% ZINC HEX-CEM" (a zinc carboxylate salt of 2-ethylhexanoic acid with 99% purity; commercial product contains 99 percent by weight zinc carboxylate salt and 1 percent by weight diethylene glycol dimethylether, obtained from OMG Americas, Inc., Westlake, Ohio). The mixture was heated to 130° C. and stirred at atmospheric pressure under N$_2$. 66.9 grams (0.300 moles) of VESTANAT® IPDI was then added to the reaction mixture. An exotherm to 136° C. and evolution of gas from the reaction mixture were observed. The reaction temperature was then raised to and maintained at 130° C. for 6 hours. The Fourier Transform Infrared Spectroscopy (FT-IR) of the final product showed the absence (disappearance) of a peak around 2285 cm$^{-1}$ (NCO) and the appearance of a peak around 1650 cm$^{-1}$ (CONH). The final product was a translucent solid resin at room temperature having the following properties: acid number 13.2; viscosity at 135° C. 129.7 centipoise (as measured by a Ferranti-Shirley cone-plate viscometer); melting points 98.3° C. and 105.8° C. (as measured by differential scanning calorimetery using a DUPONT 2100 calorimeter at a scan rate of 20° C. per minute). It is believed that a major product of the reaction (in addition to minor amounts of diamide products) was a tetra-amide of the formula

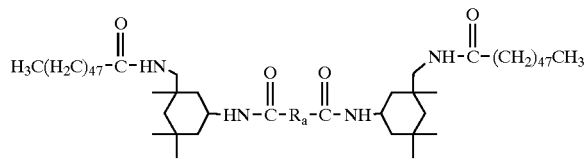

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; at least some isomers of the tetra-amide product were believed to be of the formula

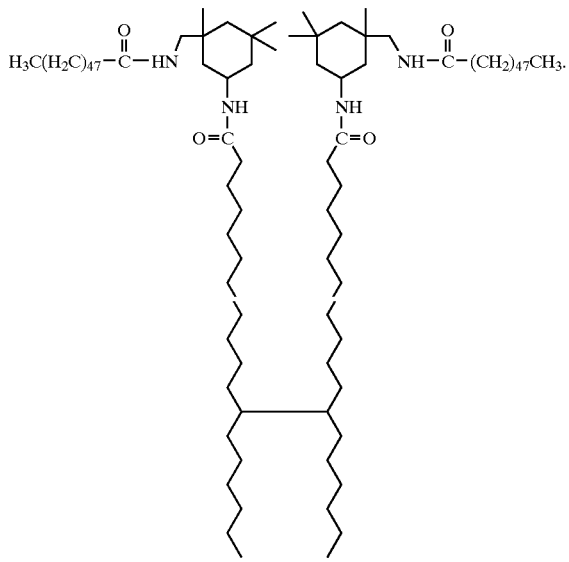

EXAMPLE V

To a 1,000 milliliter four-neck roundbottom flask fitted with a TRUBORE stirrer, $N_2$ inlet and outlet, and thermocouple-temperature controller was added 57.3 grams (0.100 moles) of PRIPOL 1006, 186.0 grams (0.208 moles) of UNICID 700, and 135.1 grams of POLYWAX PE655 (polyethylene wax, obtained from Baker-Petrolite Co., Tulsa, Okla., of the formula $CH_3(CH_2)_{50}CH_3$). The mixture was heated to 120° C. and stirred at atmospheric pressure under $N_2$. 1.35 grams of "22% ZINC HEX-CEM" and 44.4 grams (0.200 moles) of VESTANAT® IPDI were then added to the reaction mixture. An exotherm to 121° C. and evolution of gas from the reaction mixture were observed. The reaction temperature was maintained at 120° C. for 6 hours. The Fourier Transform Infrared Spectroscopy (FT-IR) of the final product showed the absence (disappearance) of a peak around 2285 cm$^{-1}$ (NCO) and the appearance of a peak around 1650 cm$^{-1}$ (CONH). The final product was a translucent solid resin at room temperature having the following properties: acid number 14.9; viscosity at 135° C. 48.8 centipoise (as measured by a Ferranti-Shirley cone-plate viscometer); melting points 96.0° C. and 103.0° C. (as measured by differential scanning calorimetry using a DUPONT 2100 calorimeter at a scan rate of 20° C. per minute). It is believed that a major product of the reaction (in addition to minor amounts of diamide products) was a tetra-amide of the formula

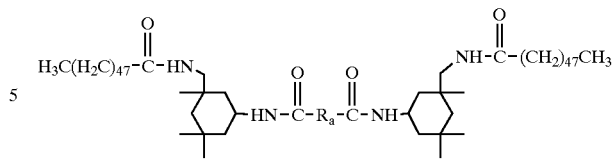

wherein $R_a$ is a branched alkylene group having about 34 carbon atoms and which may include unsaturations and cyclic groups, more specifically a group of the formula $C_{34}H_{62+n}$ wherein n is an integer of 0, 1, 2, 3, 4, 5, 6, 7, 8, 9, or 10; at least some isomers of the tetra-amide product were believed to be of the formula

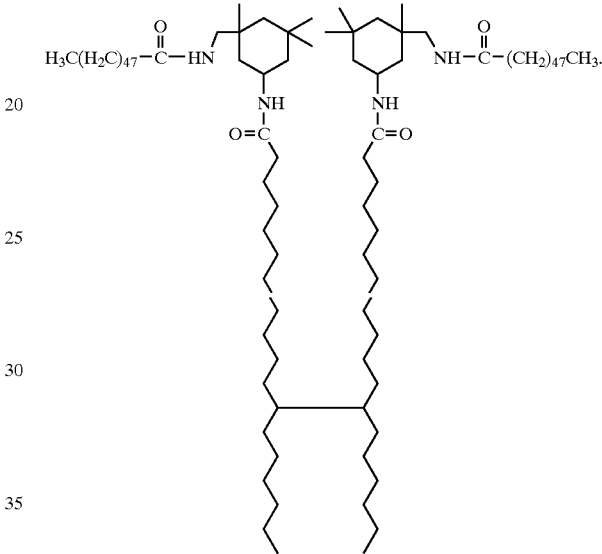

INK EXAMPLE 1

In a stainless steel beaker were combined 200 grams of the tetra-amide-containing reaction product prepared as described in Example I and 478 grams of POLYWAX PE655 (polyethylene wax, obtained from Baker-Petrolite Co., Tulsa, Okla., of the formula $CH_3(CH_2)_{50}CH_3$). To this beaker were added 81 grams of a diurethane resin prepared as described in Example I of U.S. Pat. No. 5,830,942, the disclosure of which is totally incorporated herein by reference. In addition, 1.44 grams of NAUGUARD® 445 antioxidant (obtained from Uniroyal Chemical Co., Middlebury, Conn.) was added to the mixture. The materials were melted together at a temperature of 135° C. in an oven, then blended by stirring in a temperature-controlled mantle for 0.5 hour at 135° C. Thereafter, 38.88 grams of a cyan wax prepared as described in Example 4 of U.S. Pat. No. 5,919,839, the disclosure of which is totally incorporated herein by reference, was added to the mixture and the mixture was stirred for an additional 2 hours. Subsequently, 10 grams of HYFLO SUPERCEL filter aid (obtained from Fluka Chemical) was added and stirred into the molten ink for 5 minutes. The ink was then filtered through a heated (135° C.) Mott apparatus (obtained from Mott Metallurgical) using Whatman #3 filter paper at 15 psi. The filtered ink was then poured into molds and allowed to solidify to form ink sticks. This final cyan ink product had a viscosity of 11.8 centipoise at 135° C. as measured by a Rheometric Scientific RS-2000 cone-plate viscometer and a melting point of 91° C. as measured by differential scanning calorimetry using a DUPONT 2100 calorimeter. The glass transition temperature ($T_g$) was 10° C. as measured by dynamic mechanical analysis using a Rheometric Scientific RSA II Solids Analyzer. The spectral strength of the ink was determined in butanol to be 1,400 mL·A/g using a Perkin-Elmer Lambda 2S UV/VIS spectrophotometer. This ink was placed in a XEROX® PHASER 840 printer and the ink was printed using a printhead temperature of 135° C. The finished prints were found to have a coefficient of friction against glass of 0.48 as measured by a Thwing-Albert Friction/Peel Tester (Model 225-1).

INK EXAMPLE 2

In a stainless steel beaker were combined 132 grams of the tetra-amide-containing reaction product prepared as described in Example I and 428 grams of POLYWAX PE655 (polyethylene wax, obtained from Baker-Petrolite Co., Tulsa, Okla., of the formula $CH_3(CH_2)_{50}CH_3$). To this beaker were added 73.36 grams of a diurethane resin prepared as described in Example I of U.S. Pat. No. 5,830,942, the disclosure of which is totally incorporated herein by reference. In addition, 27 grams of a triurethane wax prepared as described in Example 4 of U.S. Pat. No. 6,309,453, the disclosure of which is totally incorporated herein by reference, and 19.4 grams of SANTICIZER 278, a plasticizer obtained from Solutia (formerly Monsanto Company, St. Louis, Mo.). In addition, 1.44 grams of NAUGUARD® 445 antioxidant (obtained from Uniroyal Chemical Co., Middlebury, Conn.) was added to the mixture. The materials were melted together at a temperature of 135° C. in an oven, then blended by stirring in a temperature-controlled mantle for 0.5 hour at 135° C. Thereafter, 22.5 grams of SAVINYL BLACK NS dye (obtained from Clariant Corp., Coventry, R.I.) was added to the mixture and the mixture was stirred for an additional 2 hours. Subsequently, 10 grams of HYFLO SUPERCEL filter aid (obtained from Fluka Chemical) was added and stirred into the molten ink for 5 minutes. The ink was then filtered through a heated (135° C.) Mott apparatus (available from Mott Metallurgical) using Whatman #3 filter paper at 5 psi. The filtered ink was then poured into molds and allowed to solidify to form ink sticks. This final black ink product had a viscosity of 12.0 centipoise at 135° C. as measured by a Rheometric Scientific RS-2000 cone-plate viscometer. The glass transition temperature ($T_g$) was 0° C. as measured by dynamic mechanical analysis using a Rheometric Scientific RSA 11 Solids Analyzer. The spectral strength of the ink was determined in butanol to be 794 mL·A/g using a Perkin-Elmer Lambda 2S UV/VIS spectrophotometer. This ink was placed in a XEROX® PHASER 840 printer and printed using a printhead temperature of 135° C. The finished prints were found to have a coefficient of friction against glass of 0.33 as measured by a Thwing-Albert Friction/Peel Tester (Model 225-1).

INK EXAMPLE 3

In a stainless steel beaker were combined 163 grams of the tetra-amide-containing reaction product prepared as described in Example I, 347 grams of POLYWAX PE655 (polyethylene wax, obtained from Baker-Petrolite Co., Tulsa, Okla., of the formula $CH_3(CH_2)_{50}CH_3$), and 138 grams of stearyl stearamide (KEMAMIDE S-180, obtained from Witco, Memphis, Tenn.). In addition were added 99.4 grams of a diurethane resin prepared as described in Example I of U.S. Pat. No. 5,830,942, the disclosure of which is totally incorporated herein by reference, and 27 grams of a triurethane wax prepared as described in Example 4 of U.S. Pat. No. 6,309,453, the disclosure of which is totally incorporated herein by reference. In addition, 1.68 grams of NAUGUARD® 445 antioxidant (obtained from Uniroyal Chemical Co., Middlebury, Conn.) was added to the mixture. The materials were melted together at a temperature of 135° C. in an oven, then blended by stirring in a temperature-controlled mantle for 0.5 hour at 135° C. Thereafter, 3.76 grams of NEPTUN RED BASE NB dye (obtained from BASF Corp., Rensselaer, N.Y.), 3.76 grams of Keyplast Magenta RB dye (obtained from Keystone Aniline Corp., Chicago, Ill.), and 2.0 grams of BIO-SOFT S-100 (dodecylbenzenesulfonic acid, obtained from Stepan Company, Northfield, Ill.) were added to the mixture and the mixture was stirred for an additional 2 hours. Subsequently, 10 grams of HYFLO SUPERCEL filter aid (obtained from Fluka Chemical) was added and stirred into the molten ink for 5 minutes. The ink was then filtered through a heated (135° C.) Mott apparatus (available from Mott Metallurgical) using Whatman #3 filter paper at 5 psi. The filtered ink was poured into molds and allowed to solidify to form ink sticks. This final magenta ink product had a viscosity of 11.8 centipoise at 135° C. as measured by a Rheometric Scientific RS-2000 cone-plate viscometer. This ink was placed in a Phaser 840 printer and printed using a printhead temperature of 135° C. The finished prints were found to have a coefficient of friction against glass of 0.35 as measured by a Thwing-Albert Friction/Peel Tester (Model 225-1).

INK EXAMPLE 4

In a stainless steel beaker were combined 138 grams of the tetra-amide-containing reaction product prepared as described in Example I and 493 grams of POLYWAX PE655 (polyethylene wax, obtained from Baker-Petrolite Co., Tulsa, Okla, of the formula $CH_3(CH_2)_{50}CH_3$). To this beaker were added 115 grams of a diurethane resin prepared as described in Example I of U.S. Pat. No. 5,830,942, the disclosure of which is totally incorporated herein by reference, and 41 grams of a triurethane wax prepared as described in Example 4 of U.S. Pat. No. 6,309,453, the disclosure of which is totally incorporated herein by reference. In addition, 1.68 grams of NAUGUARD® 445 antioxidant (obtained from Uniroyal Chemical Co., Middlebury, Conn.) was added to the mixture. The materials were melted together at a temperature of 135° C. in an oven, then blended by stirring in a temperature-controlled mantle for 0.5 hour at 135° C. Thereafter, 12.0 grams of Orasol Yellow 2GLN dye (obtained from Ciba Specialty Chemicals, Newport, Del.) was added to the mixture and the mixture was stirred for an additional 2 hours. Subsequently, 10 grams of HYFLO SUPERCEL filter aid (obtained from Fluka Chemical) was added and stirred into the molten ink for 5 minutes. The ink was then filtered through a heated (135° C.) Mott apparatus (obtained from Mott Metallurgical) using Whatman #3 filter paper at 5 psi. The filtered ink was then poured into molds and allowed to solidify to form ink sticks. This final yellow ink product has a viscosity of 11.8 centipoise at 135° C. as measured by a Rheometric Scientific RS-2000 cone-plate viscometer. This ink was placed in a XEROX® PHASER 840 printer and printed using a printhead temperature of 135° C. The finished prints were found to have a coefficient of friction against glass of 0.35 as measured by a Thwing-Albert Friction/Peel Tester (Model 225-1).

INK TESTING

The inks of Ink Examples 1, 2, 3 and 4 were printed using a XEROX® PHASER 840 color printer on 24 pound HAM- MERMILL Laser Print paper. The following aspects of printed performance were determined: automatic document feed efficiency (ADF), fold durability, blocking transfer, and adhesion to transparency film. Automatic document feed index (ADF) represents an efficiency equal to the number of successful prints through a test fixture divided by the number of prints within the test suite. Fold durability represents the crease width (mils) of a solid fill print perpendicular to the machine direction determined by first passing the print through a DUPLO D-590 paper folder, followed by measuring the resulting crease width on an OLYMPUS SZH10 optical microscope equipped with a SEMPREX x-y micrometer stage. Blocking transfer is a measure of ink offset determined as described in *IS&T NIP* 12: *Intl. Conference on Digital Printing Technologies*, (1996), 56–59, the disclosure of which is totally incorporated herein by reference. Kink is a relative measure of ink adhesion to a transparency media, typically, 3M CG3300 Transparency Film for Laser Printers.

Solid field images with a resolution of 450 dpi×600 dpi were generated from the printer, and their color space data were obtained on an ACS® Spectro Sensor® II Colorimeter (obtained from Applied Color Systems Inc.) in accordance with the measuring methods stipulated in ASTM 1E805 (Standard Practice of Instrumental Methods of Color or Color Difference Measurements of Materials) using the appropriate calibration standards supplied by the instrument manufacturer. For purposes of verifying and quantifying the overall colorimetric performance of the inks, measurement data were reduced, via tristimulus integration, following ASTM E308 (Standard Method for Computing the Colors of Objects using the CIE System) in order to calculate the 1976 CIE L* (Lightness), a* (redness-greenness), and b* (yellowness-blueness) CIELAB values for each phase change ink sample.

A summary of the image feed reliability, durability and printed color performance is listed in the following table:

| color | cyan | magenta | yellow | black |
|-------|------|---------|--------|-------|
| ADF   | excellent | good | excellent | excellent |
| fold  | 23.8 | —    | 27.2   | 23.0  |
| block | 0.02 | 0.02 | 0.01   | 0.01  |
| kink  | good | good | good   | very good |
| L*    | 50.34 | 56.5 | 83.7  | 25.5  |
| a*    | −15.7 | 71.8 | −0.6  | 1.9   |
| b*    | −41.8 | −28.3 | 80.2 | −4.0  |

— = not determined

Other embodiments and modifications may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A process for preparing a phase change ink composition which comprises (a) carrying out a condensation reaction between a diacid, a monoacid, and a diisocyanate, thereby forming a tetra-amide; and (b) admixing the tetra-amide thus formed with a colorant, thereby forming a phase change ink.

2. A process according to claim 1 wherein the tetra-amide and the colorant are further admixed with a polyethylene wax.

3. A process according to claim 1 wherein the tetra-amide and the colorant are further admixed with a monoamide.

4. A process according to claim 1 wherein the tetra-amide and the colorant are further admixed with a urethane resin.

5. A process according to claim 1 wherein the tetra-amide is present in the ink in an amount of at least about 10 percent by weight of the ink and in an amount of no more than about 32 percent by weight of the ink, and wherein the tetra-amide and the colorant are further admixed with (i) a polyethylene wax, present in the ink in an amount of at least about 25 percent by weight of the ink and in an amount of no more than about 60 percent by weight of the ink; (ii) a stearyl stearamide wax, present in the ink in an amount of at least about 8 percent by weight of the ink and in an amount of no more than about 32 percent by weight of the ink; (iii) a urethane resin derived from the reaction of two equivalents of hydroabietyl alcohol and one equivalent of isophorone diisocyanate, present in the ink in an amount of at least about 6 percent by weight of the ink and in an amount of no more than about 16 percent by weight of the ink; (iv) a urethane resin that is the adduct of three equivalents of stearyl isocyanate and a glycerol-based alcohol, present in the ink in an amount of at least about 2 percent by weight of the ink and in an amount of no more than about 13 percent by weight of the ink; and (v) an antioxidant, present in the ink in an amount of at least about 0.01 percent by weight of the ink and in an amount of no more than about 1 percent by weight of the ink.

6. A process according to claim 1 wherein the tetra-amide is present in the ink in an amount of at least about 13 percent by weight of the ink and in an amount of no more than about 27 percent by weight of the ink, and wherein the tetra-amide and the colorant are further admixed with (i) a polyethylene wax, present in the ink in an amount of at least about 30 percent by weight of the ink and in an amount of no more than about 53 percent by weight of the ink; (ii) a stearyl stearamide wax, present in the ink in an amount of at least about 10 percent by weight of the ink and in an amount of no more than about 28 percent by weight of the ink; (iii) a urethane resin derived from the reaction of two equivalents of hydroabietyl alcohol and one equivalent of isophorone diisocyanate, present in the ink in an amount of at least about 8 percent by weight of the ink and in an amount of no more than about 14 percent by weight of the ink; (iv) a urethane resin that is the adduct of three equivalents of stearyl isocyanate and a glycerol-based alcohol, present in the ink in an amount of at least about 3 percent by weight of the ink and in an amount of no more than about 10 percent by weight of the ink; and (v) an antioxidant, present in the ink in an amount of at least about 0.05 percent by weight of the ink and in an amount of no more than about 0.5 percent by weight of the ink.

7. A process according to claim 1 wherein the tetra-amide is present in the ink in an amount of at least about 16 percent by weight of the ink and in an amount of no more than about 22 percent by weight of the ink, and wherein the tetra-amide and the colorant are further admixed with (i) a polyethylene wax, present in the ink in an amount of at least about 37 percent by weight of the ink and in an amount of no more than about 48 percent by weight of the ink; (ii) a stearyl stearamide wax, present in the ink in an amount of at least about 12 percent by weight of the ink and in an amount of no more than about 25 percent by weight of the ink; (iii) a urethane resin derived from the reaction of two equivalents of hydroabietyl alcohol and one equivalent of isophorone diisocyanate, present in the ink in an amount of at least about 10 percent by weight of the ink and in an amount of no more than about 12 percent by weight of the ink; (iv) a urethane resin that is the adduct of three equivalents of stearyl isocyanate and a glycerol-based alcohol, present in the ink in an amount of at least about 4.5 percent by weight of the ink and in an amount of no more than about 7.5 percent by weight of the ink; and (v) an antioxidant, present in the ink in an amount of at least about 0.1 percent by weight of the ink and in an amount of no more than about 0.3 percent by weight of the ink.

8. A process according to claim 1 wherein the colorant is present in the ink in an amount of at least about 0.1 percent by weight of the ink.

9. A process according to claim 1 wherein the colorant is present in the ink in an amount of no more than about 10 percent by weight of the ink.

10. A process according to claim 1 wherein the ink has a melting point of no lower than about 50° C.

11. A process according to claim 1 wherein the ink has a melting point of no lower than about 70° C.

12. A process according to claim 1 wherein the ink has a melting point of no lower than about 80° C.

13. A process according to claim 1 wherein the ink has a melting point of no higher than about 160° C.

14. A process according to claim 1 wherein the ink has a melting point of no higher than about 140° C.

15. A process according to claim 1 wherein the ink has a melting point of no higher than about 100° C.

16. A process according to claim 1 wherein the ink has a viscosity at jetting temperatures of no more than about 30 centipoise.

17. A process according to claim 1 wherein the ink has a viscosity at jetting temperatures of no more than about 20 centipoise.

18. A process according to claim 1 wherein the ink has a viscosity at jetting temperatures of no more than about 15 centipoise.

19. A process according to claim 1 wherein the ink has a viscosity at jetting temperatures of no less than about 2 centipoise.

20. A process according to claim 1 wherein the ink has a viscosity at jetting temperatures of no less than about 5 centipoise.

21. A process according to claim 1 wherein the ink has a viscosity at jetting temperatures of no less than about 7 centipoise.

22. A process for preparing a tetra-amide which comprises carrying out a condensation reaction between a diacid, a monoacid, and a diisocyanate, thereby forming a tetra-amide.

23. A process according to claim 22 wherein the diacid is of the formula

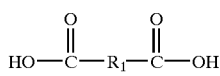

wherein $R_1$ is an alkylene group, an arylene group, an arylalkylene group, or an alkylarylene group.

24. A process according to claim 23 wherein $R_1$ is an unsubstituted alkylene group, an unsubstituted arylene group, an unsubstituted arylalkylene group, or an unsubstituted alkylarylene group.

25. A process according to claim 23 wherein $R_1$ is a substituted alkylene group, a substituted arylene group, a substituted arylalkylene group, or a substituted alkylarylene group.

26. A process according to claim 23 wherein $R_1$ is an alkylene group having hetero atoms therein, an arylene group having hetero atoms therein, an arylalkylene group having hetero atoms therein, or an alkylarylene group having hetero atoms therein, provided that no hetero atoms are directly bonded to either of the carboxylic acid groups.

27. A process according to claim 23 wherein $R_1$ is an alkylene group having no hetero atoms therein, an arylene group having no hetero atoms therein, an arylalkylene group having no hetero atoms therein, or an alkylarylene group having no hetero atoms therein.

28. A process according to claim 23 wherein $R_1$ is a branched alkylene group having at least about 34 carbon atoms.

29. A process according to claim 23 wherein $R_1$ is a branched alkylene group having about 34 carbon atoms and which may include unsaturations and cyclic groups.

30. A process according to claim 23 wherein $R_1$ is a branched alkylene group of the formula $C_{34}H_{62+n}$ wherein n is an integer of 0, 1, 2, 3, 4, 5, 6, 7, 8, 9, or 10.

31. A process according to claim 22 wherein the diacid is of the formula

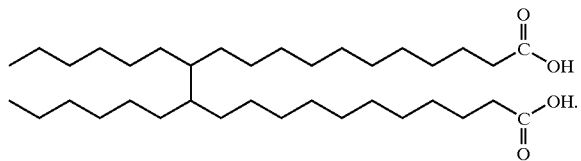

32. A process according to claim 22 wherein the diacid is malonic acid, methyl malonic acid, ethyl malonic acid, butyl malonic acid, dimethyl malonic acid, diethyl malonic acid, succinic acid, methyl succinic acid, dimethyl succinic acid, 2-ethyl-2-methyl succinic acid, 2,3-dimethyl succinic acid, glutaric acid, 2-methyl glutaric acid, 3-methyl glutaric acid, 2,2-dimethyl glutaric acid, 3,3-dimethyl glutaric acid, adipic acid, 3-methyl adipic acid, 3-tert-butyl adipic acid, pimelic acid, suberic acid, azelaic acid, sebacic acid, 1,11-undecanedicarboxylic acid, undecanedioic acid, 1,10-decanedicarboxylic acid, 1,12-dodecanedicarboxylic acid, hexadecanedioic acid, docosanedioic acid, tetracosanedioic acid, itaconic acid, maleic acid, fumaric acid, citraconic acid, mesaconic acid, glutaconic acid, β-hydromuconic acid, traumatic acid, muconic acid, aconitic acid, chlorosuccinic acid, bromosuccinic acid, 2,3-dibromosuccinic acid, tetrafluorosuccinic acid, hexafluoroglutaric acid, perfluoroadipic acid, perfluorosuberic acid, 3-chlorododecanedioic acid, dibromomaleic acid, diglycolic acid, 3,6-dioxaoctanedioic acid, thiodiglycolic acid, 3,3'-thiodipropionic acid, 1,3-acetonedicarboxylic acid, 3-oxoadipic acid, 4-ketopimelic acid, 5-oxoazelaic acid, chelidonic acid, 1,2-cyclopentanedicarboxylic acid, 3,3-tetramethyleneglutaric acid, camphoric acid, cyclohexylsuccinic acid, 1,1-cyclohexanediacetic acid, 1,2-cyclohexanedicarboxylic acid, 1,3-cyclohexanedicarboxylic acid, 1,4-cyclohexanedicarboxylic acid, 1,3-adamantanedicarboxylic acid, 1,3-adamantanediacetic acid, 5-norbornene-2,3-dicarboxylic acid, 1,4,5,6,7,7-hexachloro-5-norbornene-2,3-dicarboxylic acid, phenylsuccinic acid, 3-phenylglutaric acid, 1,2-phenylenediacetic acid, 1,2-phenylenedioxydiacetic acid, homophthalic acid, 1,3-phenylenediacetic acid, 4-carboxyphenoxyacetic acid, 1,4-phenylenediacetic acid, 1,4-phenylenedipropionic acid, 2-carboxycinnamic acid, 1,4-phenylenediacrylic acid, 2-carboxybenzenepropanoic acid, 4,4'-(hexafluoroisopropylidene)bis(benzoic acid), 4,4'-oxybisfbenzoic acid), phthalic acid, isophthalic acid, terephthalic acid, 3-fluorophthalic acid, 2-methoxyisophthalic acid, 3-nitrophathalic acid, 4-methylphthalic acid, 2-bromoterephthalic acid, 4-bromoisophthalic acid, 4-nitrophthalic acid, nitroterephthalic acid, 5-tert-butylisophthalic acid, 5-octadecyloxyisophthalic acid, 5-nitroisophthalic acid, 4,5-dichlorophthalic acid, tetrafluoroterephthalic acid, tetrafluoroisophthalic acid, tetrafluorophthalic acid, diphenic acid, 4,4'-biphenyldicarboxylic acid, 4-[4-(2-carboxybenzoyl)phenyl]butyric acid, 1,4-naphthalenedicarboxylic acid, 2,3-naphthalenedicarboxylic acid, 2,6-naphthalenedicarboxylic acid, 2,7-di-tert-butyl-9, 9-dimethyl-4,5-xanthenedicarboxylic acid, phenylmalonic acid, benzylmalonic acid, or mixtures thereof.

33. A process according to claim 22 wherein the monoacid is of the formula

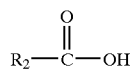

wherein $R_2$ is an alkyl group, an aryl group, an arylalkyl group, or an alkylaryl group.

34. A process according to claim 33 wherein $R_2$ is an unsubstituted alkyl group, an unsubstituted aryl group, an unsubstituted arylalkyl group, or an unsubstituted alkylaryl group.

35. A process according to claim 33 wherein $R_2$ is a substituted alkyl group, a substituted aryl group, a substituted arylalkyl group, or a substituted alkylaryl group.

36. A process according to claim 33 wherein $R_2$ is an alkyl group having hetero atoms therein, an aryl group having hetero atoms therein, an arylalkyl group having hetero atoms therein, or an alkylaryl group having hetero atoms therein, provided that no hetero atoms are directly bonded to the carboxylic acid group.

37. A process according to claim 23 wherein $R_1$ is an alkylene group having no hetero atoms therein, an arylene group having no hetero atoms therein, an arylalkylene group having no hetero atoms therein, or an alkylarylene group having no hetero atoms therein.

38. A process according to claim 22 wherein the monoacid is acetic acid, propionic acid, butyric acid, valeric acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, eicosanoic acid, heneicosanoic acid, docosanoic acid, tricosanoic acid, tetracosanoic acid, hexacosanoic acid, heptacosanoic acid, octacosanoic acid, triacontanoic acid, isobutyric acid, 2-ethylbutyric acid, trimethylacetic acid, 2-methylbutyric acid, isovaleric acid, 2,2-dimethylbutyric acid, tert-butylacetic acid, 2-methylvaleric acid, 2-propylpentanoic acid, 3-methylvaleric acid, 4-methylvaleric acid, 2-methylhexanoic acid, 2-ethylhexanoic acid, acrylic acid, methacrylic acid, crotonic acid, vinylacetic acid, tiglic acid, 3,3-dimethylacrylic acid, 2-pentenoic acid, 4-pentenoic acid, 2-methyl-2-pentenoic acid, 2,2-dimethyl-4-pentenoic acid, 2-hexenoic acid, 3-hexenoic acid, 2-ethyl-2-hexenoic acid, 6-heptenoic acid, 2-octenoic acid, citronellic acid, undecylenic acid, myristoleic acid, palmitoleic acid, oleic acid, elaidic acid, 11-eicosenoic acid, erucic acid, nervonic acid, chloroacetic acid, bromoacetic acid, iodoacetic acid, difluoroacetic acid, dichloroacetic acid, dibromoacetic acid, trifluoroacetic acid, chlorodifluoroacetic acid, trichloroacetic acid, tribromoacetic acid, 2-chloropropionic acid, 3-chloropropionic acid, 2-bromopropionic acid, 3-bromopropionic acid, 2-iodopropionic acid, 3-iodopropionic acid, 2,2-dichloropropionic acid, 2,3-dibromopropionic acid, pentafluoropropionic acid, 2-bromo-2-methylpropionic acid, 3-bromo-2-(bromomethyl)-propionic acid, 3-chloropivalic acid, 3,3-dichloropivalic acid, 4-chlorobutyric acid, 2-bromobutyric acid, 4-bromobutyric acid, heptafluorobutyric acid, 2-bromo-3-methylbutyric acid, 5-chlorovaleric acid, 2-bromovaleric acid, 5-bromovaleric acid, nonafluoropentanoic acid, 2-bromohexanoic acid, 6-bromohexanoic acid, tridecafluoroheptanoic acid, 2-bromooctanoic acid, 8-brommooctanoic acid, pentadecafluorooctanoic acid, heptadecafluorononanoic acid, nonadecafluorodecanoic acid, perfluorosebacic acid, 11-bromoundecanoic acid, 12-bromododecanoic acid, perfluorododecanoic acid, 2-bromotetradecanoic acid, 2-bromohexadecanoic acid, 3-chloroacrylic acid, 2-bromoacrylic acid, 2-(trifluoromethyl)acrylic acid, 2-(bromomethyl)acrylic acid, 4,4,4-trifluoro-3-methyl-2-butenoic acid, methoxyacetic acid, ethoxyacetic acid, 3-methoxypropionic acid, 2-(2-methoxyethoxy)acetic acid, 2-[2-(methoxyethoxy)ethoxy] acetic acid, tetrahydro-2-furoic acid, tetrahydro-3-furoic acid, 2,3,4,6-di-O-isopropylidene-2-ketogluconic acid, 3-nitropropionic acid, 6-nitrocaproic acid, 1 2-nitrododecanoic acid, succinic semialdehyde, levulinic acid, 4-acetylbutyric acid, 6-oxoheptanoic acid, 7-oxooctanoic acid, 4,6-dioxoheptanoic acid, 3,4-dihydro-2,2-dimethyl-4-oxo-2H-pyran-6-carboxylic acid, cyclopentanecarboxylic acid, cyclopentylacetic acid, 3-cyclopentylpropionic acid, 3-methyl-2-(nitromethyl)-5-oxocyc/opentaneacetic acid, cyciohexanecarboxylic acid, cyclohexylacetic acid, dicyclohexylacetic acid, cyclohexanepropionic acid, cyclohexanebutyric acid, cyclohexanepentanoic acid, 1-methyl-1-cyclohexanecarboxylic acid, 2-methyl-1-cyclohexanecarboxyic acid, 3-methyl-1-cyclohexanecarboxylic acid, 4-methyl-1-cyclohexanecarboxylic acid, 4-tert-butylcyclohexanecarboxylic acid, 4-pentylcyclohexanecarboxylic acid, 4-methylcyclohexaneacetic acid, 3-methoxycyclohexanecarboxylic acid, 4-methoxycyclohexanecarboxylic acid, cyclohexanecarboxylic acid, 2-norbornaneacefic acid, 4-pentylbicyclo [2.2.2]octane-1-carboxylic acid, 3-oxotricyclo[2.2.1.0(2,6)]-heptane-1-carboxylic acid, 3-noradamantanecarboxylic acid, 1-adamantanecarboxylic acid, 1-adamantaneacetic acid, 1-cyclopentene-1-carboxylic acid, 2-cyclopentene-1-acetic acid, 1-cyclohexene-1-carboxylic acid, 1-methyl-2-cyclohexene-1-carboxylic acid, 1,4-dihydro-2-methylbenzoic acid, retinoic acid, ketopinic acid, abietic acid, phenylacetic acid, 1-phenyl-1-cyclopentanecarboxylic acid, α-phenylcyclopentaneacetic acid, diphenylacetic acid, triphenylacetic acid, 2-phenylpropionic acid, hydrocinnamic acid, α-methylhydrocinnamic acid, α-(tert-butyl) hydrocinnamic acid, 2,2-diphenylpropionic acid, 3,3-diphenylpropionic acid, 3,3,3-triphenylpropionic acid, 2-phenylbutyric acid, 3-phenylbutyric acid, 4-phenylbutyric acid, 5-phenylvaleric acid, 3-methyl-2-phenylvaleric acid, 6-phenylhexanoic acid, α-fluorophenylacetic acid, α-bromophenylacetic acid, α-methoxyphenylacetic acid, phenoxyacetic acid, α,β-dibromohydrocinnamic acid, 3-phenoxypropionic acid, 2-phenoxypropionic acid, -phenoxyundecanoic acid, 2-phenoxybutyric acid, α-methoxy-α-(trifluoromethyl) phenylacetic acid(phenylthio)acetic acid, 3-(phenylthio) acrylic acid, benzylthioglycolic acid, 2-ethylthio-2,2-diphenylacetic acid, 3-benzoylpropionic acid, 2-methyl-4-oxo-4-phenylbutyric acid, 4-benzoylbutyric acid, o-tolylacetic acid, 3-oxo-1-indancarboxylic acid, 1,2,3,4-tetrahydro-2-naphthoic acid, (α,α,α-trifluoro-o-tolyl)acetic acid, 2-fluorophenylacetic acid, 2-chlorophenylacetic acid, 2-bromophenylacetic acid, 2-iodophenylacetic acid, 2-(2-chlorophenoxy)propionic acid, 2-methoxyphenylacetic acid, 3-(2-methoxyphenyl)propionic acid, 2-nitrophenylacetic acid, 2-formylphenoxyacetic acid, m-tolylacetic acid, 3-fluorophenylacetic acid, 3-chlorophenylacetic acid, 3-bromophenylacetic acid, 2-(3-chlorophenoxy)propionic acid, (α,α,α-trifluoro-m-tolyl)acetic acid, 3-methoxyphenylacetic acid, 3-nitrophenylacetic acid, p-tolylacetic acid, 3-(p-tolyl)propionic acid, (4-methylphenoxy)acetic acid, 4-isobutyl-α-methylphenylacetic acid, 4-acetylphenoxyacetic acid, 4-(4-chloro-o-tolyloxy)butyric acid, 4-fluorophenylacetic acid, (α,α,α-trifluoro-p-tolyl)acetic acid, 3-(4-fluorobenzoyl)propionic acid, 3-(4-chlorobenzoyl)propionic acid, 4-chlorophenylacetic acid, bis(4-chlorophenyl)acetic acid, 4-bromophenylacetic acid, 3,3,3-tris(4-chlorophenyl)propionic acid, 4-(bromomethyl)phenylacetic acid, 1-(4-chlorophenyl)-1-cyclopentanecarboxylic acid, 4-methoxyphenylacetic acid, 4-ethoxyphenylacetic acid, 3-(4-methoxyphenyl)propionic acid, 4-(4-methoxyphenyl)propionic acid, 4-chlorophenoxyacetic acid, bis(4-chlorophenoxy)acetic acid, 4-(methylthio)-phenylacetic acid, 4-nitrophenylacetic acid, 2-(4-nitrophenyl) propionic acid, 4-(4-nitrophenyl)butyric acid, 3-(4-methoxybenzoyl)propionic acid, 4-fluorophenoxyacetic acid, 2-(4-chlorophenoxy)propionic acid, 2-(4-chlorophenoxy)2-methylpropionic acid, (2,4-di-tert-pentylphenoxy)acetic acid, 2,6-difluorophenylacetic acid, 2,4-difluorophenylacetic acid, 2,5-difluorophenylacetic acid, 3,5-difluorophyenylacetic acid, 4-chloro-o-tolyloxyacetic acid, 2,3-dichlorophenoxyacetic acid, 2,6-dichlorophenylacetic acid, 2,4-dichlorophenylacetic acid, 2,4-dichlorophenoxyacetic acid, 3,4-dichlorophenylacetic acid, 3,4-dichlorophenoxyacetic acid, 3,5-bis(trifluoromethyl)phenylacetic acid, 4-(2,4-di-tert-pentylphenoxy)butyric acid, 2-(2,4-dichlorophenoxy)propionic acid, 4-(2,4-dichlorophenoxy)propionic acid, 2,4,5-trichlorophenoxyacetic acid, 2-(2,4,5-trichlorophenoxy)propionic acid, (3,4-dimethoxyphenyl)acetic acid, 4-benzyloxy-3-methoxyphenylacetic acid, 3,4-(methylenedioxy)phenylacetic acid, 5-methoxy-1-indanone-3-acetic acid, 3-(3,4-dimethoxyphenyl) propionic acid, 4-(3,4-dimethoxyphenyl)butyric acid, (2,5-dimethoxyphenyl)acetic acid, 2,4-dinitrophenylacetic acid, (3,5-dimethoxyphenyl)acetic acid, 3,4,5-trimethoxyphenylacetic acid, 3-(3,4,5-trimethoxyphenyl)propionic acid, 2,3,4,5,6-pentafluorophenylacetic acid, 4-biphenylacetic acid, 1-naphthylacetic acid, 2-naphthylacetic acid, α-trityl-2-naphthalenepropionic acid, (1-naphthoxy)acetic acid, (2-naphthoxy)acetic acid, 6-methoxy-a-methyl-2-naphthaleneacetic acid, 9-fluoreneacetic acid, 1-pyreneacetic acid, 1-pyrenebutyric acid, γ-oxo-1-pyrenebutyric acid, styrylacetic acid, cinnamic acid, α-methylcinnamic acid, α-fluorocinnamic acid, α-phenylcinnamic acid, 2-methylcinnamic acid, 2-fluorocinnamic acid, 2-(trifluoromethyl)cinnamic acid, 2-chlorocinnamic acid, 2-methoxycinnamic acid, 2-nitrocinnamic acid, 3-fluorocinnamic acid, 3-(trifluoromethyl)cinnamic acid, 3-chlorocinnamic acid, 3-bromocinnamic acid, 3-methoxycinnamic acid, 3-nitrocinnamic acid, 4-methylcinnamic acid, 4-fluorocinnamiic acid, 4-(trifluoromethyl)cinnamic acid, 4-chlorocinnamic acid, 4-bromocinnamic acid, 4-methoxycinnamic acid, 4-nitrocinnamic acid, 4-formylcinnamic acid, 2,6-difluorocinnamic acid, 2,4-difluorocinnamic acid, 2,5-difluorocinnamic acid, 3,4-difluorocinnamic acid, 3,5-difluorocinnamic acid, 2-chloro-6-fluorocinnamic acid, 2,4-dichlorocinnamic acid, 3,4-dichlorocinnamic acid, 5-bromo-2-methoxycinnamic acid, 2,3-dimethoxycinnamic acid, 2,4-dimethoxycinnamic acid, 2,5-dimethoxycinnamic acid, 3,4-dimethoxycinnamic acid, 3,4-(methylenedioxy)cinnamic acid, 3,5-dimethoxycinnamic acid, 2-chloro-5-nitrocinnamic acid, 4-chloro-3-nitrocinnamic acid, 2,3,4-trifluorocinnamic acid, 3,4,5-trimethoxycinnamic acid, 2,4,5-trimethoxycinnamic acid, α-methyl-2,4,5-trimethoxycinnamic acid, 4,5-dimethoxy-2-nitrocinnamic acid, 2,3,4,5,6-pentafluorocinnamic acid, 3-methylindene-2-carboxylic acid, 3-(4-methylbenzoyl)acrylic acid, 3-(2,5-dimethylbenzoyl)acrylic acid, 3-(2,3,5,6-tetramethylbenzoyl)acrylic acid, 3-(4-methoxybenzoyl)acrylic acid, 3-(4-ethoxybenzoyl)acrylic acid, 6-methylchromone-2-carboxylic acid, benzoic acid, o-toluic acid, 2-fluorobenzoic acid, α,α,α-trifluoro-o-toluic acid, 2-chlorobenzoic acid, 2-bromobenzoic acid, 2-iodobenzoic acid, o-anisic acid, 2-ethoxybenzoic acid, 2-nitrobenzoic acid, 2-acetylbenzoic acid, 2-(p-toluoyl)benzoic acid, m-toluic acid, 3-fluorobenzoic acid, α,α,α-trifluoro-m-toluic acid, 3-chlorobenzoic acid, 3-(chloromethyl) benzoic acid, 3-bromobenzoic acid, 3-iodobenzoic acid, m-anisic acid, 3-nitrobenzoic acid, 3-carboxybenzaldehyde, p-toluic acid, 4-ethylbenzoic acid, 4-n-propylbenzoic acid, 4-isopropylbenzoic acid, 4-n-butylbenzoic acid, 4-tert-butylbenzoic acid, 4-pentylbenzoic acid, 4-hexylbenzoic acid, 4-heptylbenzoic acid, 4-octylbenzoic acid, 4-vinylbenzoic acid, 4-fluoroberzoic acid, α,α,α-trifluoro-o-toluic acid, 4-chlorobenzoic acid, 4-bromobenzoic acid, 4-iodobenzoic acid, 4-(chloromethyl) benzoic acid, α-bromo-p-toluicacid, p-anisic acid, 4-(trifluoromethoxy)benzoic acid, 4-ethoxybenzoic acid, 4-n-propoxybenzoic acid, 4-butoxybenzoic acid, 4-pentyloxybenzoic acid, 4-hexyloxybenzoic acid, 4-heptyloxybenzoic acid, 4-octyloxybenzoic acid, 4-nonyloxybenzoic acid, 4-decyloxybenzoic acid, 4-nonyloxybenzoic acid, 4-dodecyloxybenzoic acid, 4-isopropoxybenzoic acid, 4-(2-cyclohexenyloxy)benzoic acid, 4-(methylthio)benzoic acid, 4-(ethylthio)benzoic acid, 4-nitrobenzoicacid, 4-acetylbenzoic acid, 4-carboxybenzaldehyde, 2,3-dimethylbenzoic acid, 2,6-dimethylbenzoic acid, 3-fluoro-2-methylbenzoic acid, 2,3-difluorobenzoic acid, 2,6-difluorobenzoic acid, 2-fluoro-6-(trifluoromethyl)benzoic acid, 2-fluoro-3-(trifluoromethyl) benzoic acid, 2,6-bis(trifluoromethyl) benzoic acid, 2-chloro-6-fluorobenzoic acid, 2-chloro-6-fluorophenylacetic acid, 2,3-dichlorobenzoic acid, 2,6-dichlorobenzoic acid, 2,3-dimethoxybenzoic acid, 2,6-dimethoxybenzoic acid, 2-methyl-6-nitrobenzoic acid, 3-methyl-2-nitrobenzoic acid, 2-methyl-3-nitrobenzoic acid, 3-chloro-2-nitrobenzoic acid, 2-chloro-3-nitrobenzoic acid, 2-bromo-3-nitrobenzoic acid, 3-methoxy-2-nitrobenzoic acid, 3,4-dimethylbenzoic acid, 2,4-dimethylbenzoic acid, 2,5-dimethylbenzoic acid, 5-fluoro-2-methylbenzoic acid, 3-fluoro-4-methylbenzoic acid, 2-fluoro-5-methylbenzoic acid, 3-bromo-4-methylbenzoic acid, 2,4-bis(trifluoromethyl)benzoic acid, 3-iodo-4-methylbenzoic acid, 2-chloro-5-(trifluoromethyl) benzoic acid, 2,5-bis(trifluoromethyl)benzoic acid, 2,4-difluorobenzoic acid, 3,4-difluorobenzoic acid, 4-fluoro-2-(trifluoromethyl)benzoic acid, 2-fluoro-4-(trifluoromethyl) benzoic acid, 2-chloro-4-fluorobenzoic acid, 3-chloro-4-fluorobenzoic acid, 2,4-dichlorobenzoic acid, 3,4-dichlorobenzoic acid, 2,5-difluorobenzoic acid, 2,5-dichlorobenzoic acid, 3-bromo-4-fluorobenzoic acid, 5-bromo-2-chlorobenzoic acid, 3-methoxy-4-methylbenzoic acid, 3-fluoro-4-methoxybenzoic acid, 4-chloro-o-anisic acid, 5-chloro-o-anisic acid, 2-bromo-5-methoxybenzoic acid, 2,4-dimethoxybenzoic acid, 2,5-dimethoxybenzoic acid, 3,4-dimethoxybenzoic acid, 3,4-diethoxybenzoic acid, piperonylic acid, 2-chloro-5-(methylthio)benzoic acid, 2-methoxy-4-(methylthio)benzoic acid, 5-methyl-2-nitrobenzoic acid, 4-methyl-3-nitrobenzoic acid, 3-methyl-4-nitrobenzoic acid, 2-nitro-α,α,α-trifluoro-p-toluic acid, 2-fluoro-5-nitrobenzoic acid, 4-chloro-2-nitrobenzoic acid, 2-chloro-4-nitrobenzoic acid, 4-fluoro-3-nitrobenzoic acid, 4-chloro-3-nitrobenzoic acid, 5-chloro-2-nitrobenzoic acid, 2-chloro-5-nitrobenzoic acid, 2-bromo-5-nitrobenzoic acid, 4-(bromomethyl)-3-nitrobenzoic acid, 2-methoxy-4-nitrobenzoic acid, 4-methoxy-3-nitrobenzoic acid, 3-methoxy-4-nitrobenzoic acid, 5-methoxy-2-nitrobenzoic acid, 2,4-dinitrobenzoic acid, 3,5-dimethylbenzoic acid, 3,5-di-tert-butylbenzoic acid, 3,5-difluorobenzoic acid, 3,5-bis (trifluoromethyl)benzoic acid, 3,5-dichlorobenzoic acid, 3,5-dibromobenzoic acid, 3-bromo-5-iodobenzoic acid, 3,5-dimethoxybenzoic acid, 3,5-dinitrobenzoic acid, 2,3,4-trifluorobenzoic acid, 2,3,6-trifluorobenzoic acid, 2,4,6-trimethylbenzoic acid, 2,4,6-trifluorobenzoic acid, 3,4,5-trifluorobenzoic acid, 2,4,6-trichlorobenzoic acid, 2,3,5-trichlorobenzoic acid, 2,3,5-triiodobenzoic acid, 2-bromo-4, 5-dimethoxybenzoic acid, 3,4,5-trimethoxybenzoic acid, 3,4,5-triethoxybenzoic acid, 4,5-dimethoxy-2-nitrobenzoic acid, 3,5-dinitro-o-toluic acid, 3,5-dinitro-p-toluic acid, 2-chloro-3,5-dinitrobenzoic acid, 4-chloro-3,5-dinitrobenzoic acid, 2,5-dichloro-3-nitrobenzoic acid, 2,6-dichloro-3-nitrobenzoic acid, 2,3,4-trirmethoxybenzoic acid, 2,4,5-trifluorobenzoic acid, 2-chloro-4,5-difluorobenzoic acid, 2,4-dichloro-5-fluorobenzoic acid, 2,4, 5-trimethoxybenzoic acid, 2,3,4,5-tetrafluorobenzoic acid, 2,3,5,6-tetrafluorobenzoic acid, 2,4-dichloro-3,5-dinitrobenzoic acid, 2,3,5,6-tetrafluoro-p-toluic acid, 4-bromo-2,3,5,6-tetrafluorobenzoic acid, pentafluorobenzoic acid, 2-biphenylcarboxylic acid, 4'-(trifluoromethyl)-2-biphenylcarboxylic acid, 4-biphenylcarboxylic acid, 4'-ethyl-4-biphenylcarboxylic acid, 4'-octyloxy-4-biphenylcarboxylic acid, α-phenyl-o-toluic acid, 2-bibenzylcarboxylic acid, 2,3,4,5,6-pentafluorophenoxyacetic acid, 2-phenoxybenzoic acid, 3-phenoxybenzoic acid, 2-benzoylbenzoic acid, 3-benzoylbenzoic acid, 4-benzoylbenzoic acid, 2-(4-fluorobenzoyl) benzoic acid, 2-(4-chlorobenzoyl)benzoic acid, 2-(4-chloro-3-nitrobenzoyl)benzoic acid, 1-naphthoic acid, 2-naphthoic acid, 4-fluoro-1-naphtnoic acid, 2-ethoxy-1-naphthoic acid, 1,8-naphthalaldehydic acid, 2-biphenylenecarboxylic acid, γ-oxo-5-acenaphthenebutyric acid, 9-fluorenecarboxylic acid, 1-fluorenecarboxylic acid, 4-fluorenecarboxylic acid, 9-fluorenone-1-carboxylic acid, 9-fluorenone-2-carboxylic acid, 9-fluorenone-4-carboxylic acid, 7-nitro-4-fluorenecarboxylic acid, chromone-2-carboxylic acid, 9-anthracenecarboxylic acid, anthraquinone-2-carboxylic acid, xanthene-9-carboxylic acid, 1-pyrenecarboxylic acid, or mixtures thereof.

39. A process according to claim 22 wherein the monoacid is of the formula

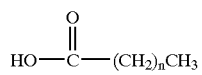

wherein n has an average value of about 36.

40. A process according to claim 22 wherein the monoacid is of the formula

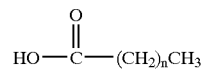

wherein n has an average value of about 46.

41. A process according to claim 22 wherein the diisocyanate is of the formula

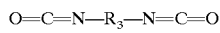

wherein $R_3$ is an alkylene group, an arylene group, an arylalkylene group, or an alkylarylene group.

42. A process according to claim 41 wherein $R_3$ is an unsubstituted alkylene group, an unsubstituted arylene group, an unsubstituted arylalkylene group, or an unsubstituted alkylarylene group.

43. A process according to claim 41 wherein $R_3$ is a substituted alkylene group, a substituted arylene group, a substituted arylalkylene group, or a substituted alkylarylene group.

44. A process according to claim 41 wherein $R_3$ is an alkylene group having hetero atoms therein, an arylene group having hetero atoms therein, an arylalkylene group having hetero atoms therein, or an alkylarylene group having hetero atoms therein, provided that no hetero atoms are directly bonded to either of the isocyanate groups.

45. A process according to claim 41 wherein $R_3$ is an alkylene group having no hetero atoms therein, an arylene group having no hetero atoms therein, an arylalkylene group having no hetero atoms therein, or an alkylarylene group having no hetero atoms therein.

46. A process according to claim 41 wherein $R_3$ is a branched alkylene group having about 34 carbon atoms.

47. A process according to claim 41 wherein $R_3$ is an alkylene group of the formula $C_{34}H_{62+n}$ wherein n is an integer of 0, 1, 2, 3, 4, 5, 6, 7, 8, 9, or 10.

48. A process according to claim 22 wherein the diisocyanate is 1,4-diisocyanatobutane, 1,6-diisocyanatohexane, 1,8-diisocyanatooctane, 1,12-diisocyanatododecane, trimethylhexamethylene diisocyanate, 1,5-diisocyanato-2-methylpentane, cyclohexylene diisocyanate, bis (isocyanatomethane) cyclohexane, 4,4'-methylenebis (cyclohexyl isocyanate), isophorone diisocyanate, phenylene diisocyanate, bis(isocyanatomethyl)benzene, bis (1-isocyanato-1-methylethyl)benzene, toluene diisocyanate, diphenylmethane-4,4'-diisocyanate, hydrogenated diphenylmethane-4,4'-diisocyanate, tetramethylxylene diisocyanate, naphthylene-1,5-diisocyanate, 3,3'-dimethoxy-4,4'-biphenyldiisocyanate, 3,3'-dimethyl-4,4'-bimethyl-4,4'-biphenyldiisocyanate, 4,4'-biphenyidiisocyanate, tetramethylene xylene diisocyanate, 4,4'-methylene % is(2,6-diethylphenyl isocyanate), 1-chloromethyl-2,4-diisocyanctobenzene, 4,4'-oxybis (phenyl isocyanate), or mixtures thereof.

49. A process according to claim 22 wherein the diisocyanate is isophorone diisocyanate or 1,6-diisocyanatohexane.

50. A process according to claim 22 wherein the diisocyanate is of the formula

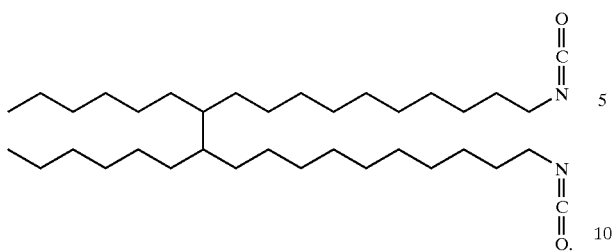

51. A process according to claim 22 wherein the diisocyanate is of the formula

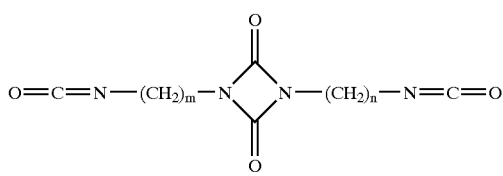

wherein m and n are each, independently of the others, integers representing the number of repeat —CH$_2$— units.

52. A process according to claim 51 wherein m and n are each 6.

53. A process according to claim 22 wherein the tetra-amide has a total number of carbon atoms of at least about 50.

54. A process according to claim 22 wherein the diacid is of the formula

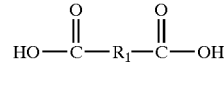

wherein R$_1$ is an alkylene group, an arylene group, an arylalkylene group, or an alkylarylene group, the monoacid is of the formula

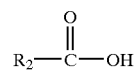

wherein R$_2$ is an alkyl group, an aryl group, an arylalkyl group, or an alkylaryl group, the diisocyanate is of the formula

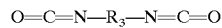

wherein R$_3$ is an alkylene group, an arylene group, an arylalkylene group, or an alkylarylene group, and the reaction proceeds as follows:

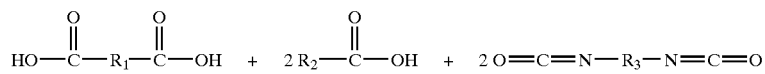

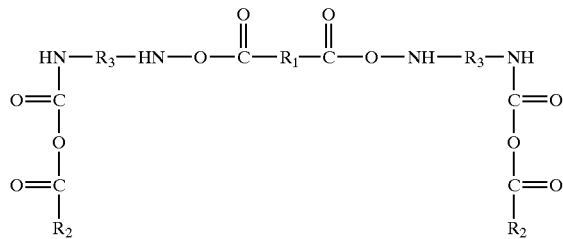

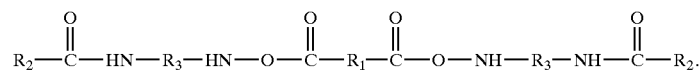

55. A process according to claim 22 wherein the diacid and the monoacid are first admixed prior to addition of the diisocyanate reactant.

56. A process according to claim 22 wherein the diacid and the monoacid are first admixed and heated prior to addition of the diisocyanate reactant.

57. A process according to claim 22 wherein the diacid, the monoacid, and a polyethylene wax are first admixed and heated prior to addition of the diisocyanate reactant.

58. A process according to claim 22 wherein the reaction takes place in an inert atmosphere.

59. A process according to claim 22 wherein the reaction mixture is heated to a temperature of at least about 60° C.

60. A process according to claim 22 wherein the reaction mixture is heated to a temperature of at least about 80° C.

61. A process according to claim 22 wherein the reaction mixture is heated to a temperature of at least about 120° C.

62. A process according to claim 22 wherein the reaction mixture is heated to a temperature of no more than about 400° C.

63. A process according to claim 22 wherein the reaction mixture is heated to a temperature of no more than about 300° C.

64. A process according to claim 22 wherein the reaction mixture is heated to a temperature of no more than about 200° C.

65. A process according to claim 22 wherein the reaction is carried out for a period of at least about 10 minutes.

66. A process according to claim 22 wherein the reaction is carried out for a period of at least about 30 minutes.

67. A process according to claim 22 wherein the reaction is carried out for a period of at least about 60 minutes.

68. A process according to claim 22 wherein the monoacid, the diacid, and the diisocyanate are present in relative amounts such that the ratio of total number of COOH groups to total number of NCO groups is at least about 1:1.

69. A process according to claim 22 wherein a catalyst is added to the reaction mixture.

70. A process according to claim 22 wherein the tetra-amide product is of the formula

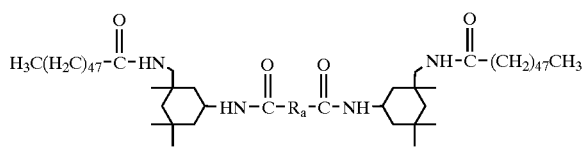

wherein $R_a$ is a branched alkylene group having about 34 carbon atoms and which may include unsaturations and cyclic groups.

71. A process according to claim 70 wherein $R_a$ is a group of the formula $C_{34}H_{62+n}$ wherein n is an integer of 0, 1, 2, 3, 4, 5, 6, 7, 8, 9, or 10.

72. A process according to claim 22 wherein the tetra-amide product is of the formula

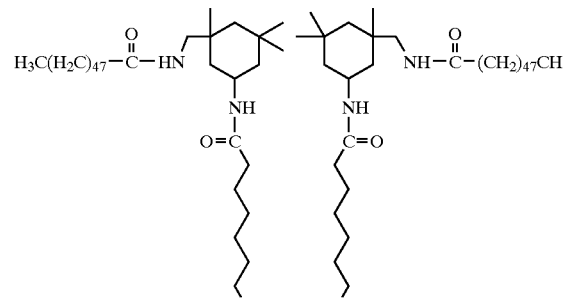

73. A process according to claim 22 wherein the tetra-amide product is of the formula

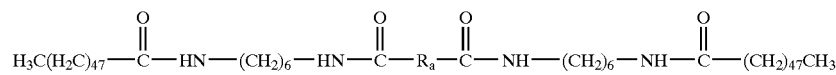

wherein $R_a$ is a branched alkylene group having about 34 carbon atoms and which may include unsaturations and cyclic groups.
74. A process according to claim 73 wherein $R_a$ is a group of the formula $C_{34}H_{62+n}$ wherein n is an integer of 0, 1, 2, 3, 4, 5, 6, 7, 8, 9, or 10.
75. A process according to claim 22 wherein the tetra-amide product is of the formula
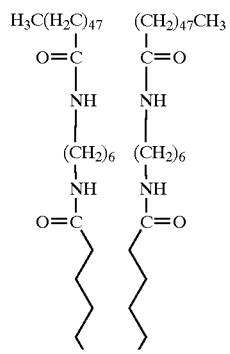
-continued
* * * * *